(12) United States Patent
Forsell

(10) Patent No.: US 8,126,558 B2
(45) Date of Patent: *Feb. 28, 2012

(54) CONTROLLED PENILE PROSTHESIS

(75) Inventor: Peter Forsell, Zug (CH)

(73) Assignee: Obtech Medical AG, Baar (CH)

( * ) Notice: Subject to any disclaimer, the term of this patent is extended or adjusted under 35 U.S.C. 154(b) by 824 days.

This patent is subject to a terminal disclaimer.

(21) Appl. No.: 11/437,771

(22) Filed: May 22, 2006

(65) Prior Publication Data

US 2006/0235482 A1 Oct. 19, 2006

Related U.S. Application Data

(63) Continuation of application No. 10/203,440, filed as application No. PCT/SE01/00309 on Feb. 14, 2001, now abandoned.

(60) Provisional application No. 60/182,189, filed on Feb. 14, 2000, provisional application No. 60/182,205, filed on Feb. 14, 2000.

(51) Int. Cl.
*A61F 2/26* (2006.01)

(52) U.S. Cl. ............................................. 607/39; 600/40

(58) Field of Classification Search .................... 600/40; 607/39

See application file for complete search history.

(56) References Cited

U.S. PATENT DOCUMENTS 2,060,913 A 11/1936 Weaver
(Continued)

FOREIGN PATENT DOCUMENTS

DE 19511998 10/1996
(Continued)

OTHER PUBLICATIONS

Publication No. EP 1568338A2, dated Aug. 31, 2005, for European Patent Application No. 05010107.0.

(Continued)

*Primary Examiner* — Michael Kahelin
(74) *Attorney, Agent, or Firm* — Nixon & Vanderhye P.C.

(57) ABSTRACT

A male sexual impotence prosthesis apparatus comprises an operable prosthesis implanted in the cavities of the corpora cavemosa of a patient's penile tissue for providing erect penile condition, when the prosthesis is operated. The prosthesis is operable by an implanted operation device. A control device is provided for controlling a source of energy, which may or may not be implanted, from outside the patient's body, to release energy for use in connection with the operation of the prosthesis, i.e., to power the operation device. The patient uses the control device to operate the prosthesis to achieve erection.

126 Claims, 7 Drawing Sheets

U.S. PATENT DOCUMENTS

| | | | |
|---|---|---|---|
| 2,795,641 A | 6/1957 | Rowell | |
| 3,209,081 A | 9/1965 | Ducote et al. | |
| 3,598,287 A | 8/1971 | De Man | |
| 3,692,027 A | 9/1972 | Ellinwood, Jr. | |
| 3,731,679 A | 5/1973 | Wilhelmson et al. | |
| 3,731,681 A | 5/1973 | Blackshear et al. | |
| 3,750,194 A | 8/1973 | Summers | |
| 3,817,237 A | 6/1974 | Bolduc | |
| 3,855,122 A | 12/1974 | Bourganel | |
| 3,875,928 A | 4/1975 | Angelchik | |
| 3,923,060 A | 12/1975 | Ellinwood, Jr. | |
| 3,954,102 A | 5/1976 | Buuck | |
| 4,003,379 A | 1/1977 | Ellinwood, Jr. | |
| 4,004,379 A | 1/1977 | Ellinwood, Jr. | |
| 4,009,711 A | 3/1977 | Uson | |
| 4,026,305 A | 5/1977 | Brownlee et al. | |
| 4,044,401 A | 8/1977 | Guiset | |
| 4,201,202 A | 5/1980 | Finney et al. | |
| 4,221,219 A | 9/1980 | Tucker | |
| 4,235,222 A | 11/1980 | Ionescu | |
| 4,243,306 A | 1/1981 | Bonini | |
| 4,246,893 A | 1/1981 | Berson | |
| 4,265,241 A | 5/1981 | Portner et al. | |
| 4,271,827 A | 6/1981 | Angelchik | |
| 4,274,407 A | 6/1981 | Scarlett | |
| 4,304,225 A | 12/1981 | Freeman | |
| 4,318,396 A | 3/1982 | Finney | |
| 4,342,308 A | 8/1982 | Trick | |
| 4,369,771 A | 1/1983 | Trick | |
| 4,400,169 A | 8/1983 | Stephen | |
| 4,407,278 A | 10/1983 | Burton et al. | |
| 4,412,530 A | 11/1983 | Burton | |
| 4,424,807 A | 1/1984 | Evans | |
| 4,505,710 A | 3/1985 | Collins | |
| 4,509,947 A | 4/1985 | Lattin | |
| 4,542,753 A | 9/1985 | Brenman et al. | |
| 4,550,720 A | 11/1985 | Trick | |
| 4,556,050 A | 12/1985 | Hodgson et al. | |
| 4,559,930 A | 12/1985 | Cobiski | |
| 4,559,939 A | 12/1985 | Cobiski | |
| 4,563,175 A | 1/1986 | Lafond | |
| 4,583,523 A | 4/1986 | Kleinke et al. | |
| 4,584,994 A | 4/1986 | Bamberger et al. | |
| 4,592,339 A | 6/1986 | Kuzmak et al. | |
| 4,592,355 A | 6/1986 | Antebi | |
| 4,599,081 A | 7/1986 | Cohen | |
| 4,602,621 A | 7/1986 | Hakky | |
| 4,610,658 A | 9/1986 | Buchwald et al. | |
| 4,623,350 A | 11/1986 | Lapeyre et al. | |
| 4,628,928 A | 12/1986 | Lowell | |
| 4,651,721 A | 3/1987 | Mikulich et al. | |
| 4,664,100 A | 5/1987 | Rudloff | |
| 4,677,534 A | 6/1987 | Okochi | |
| 4,679,560 A | 7/1987 | Galbraith | |
| 4,696,288 A | 9/1987 | Kuzmak et al. | |
| 4,699,128 A | 10/1987 | Hemmeter | |
| 4,711,231 A * | 12/1987 | Finegold et al. | 600/40 |
| 4,723,538 A | 2/1988 | Stewart et al. | |
| 4,756,949 A | 7/1988 | Spence et al. | |
| 4,771,780 A | 9/1988 | Sholder | |
| 4,828,544 A | 5/1989 | Lane et al. | |
| 4,828,990 A | 5/1989 | Higashi et al. | |
| 4,829,990 A | 5/1989 | Thuroff et al. | |
| 4,846,794 A | 7/1989 | Hertzer | |
| 4,902,279 A | 2/1990 | Schmidtz et al. | |
| 4,925,443 A | 5/1990 | Heilman et al. | |
| 4,941,461 A * | 7/1990 | Fischell | 600/40 |
| 4,942,668 A | 7/1990 | Franklin | |
| 4,958,630 A | 9/1990 | Rosenbluth et al. | |
| 4,979,955 A | 12/1990 | Smith | |
| 4,982,731 A | 1/1991 | Lue et al. | |
| 5,006,106 A | 4/1991 | Angelchik | |
| 5,012,822 A | 5/1991 | Schwarz | |
| 5,042,084 A | 8/1991 | Daly | |
| 5,048,511 A | 9/1991 | Rosenbluth et al. | |
| 5,057,075 A | 10/1991 | Moncrief et al. | |
| 5,062,416 A | 11/1991 | Stucks | |
| 5,074,868 A | 12/1991 | Kuzmak | |
| 5,088,477 A | 2/1992 | Subrini | |
| 5,098,369 A | 3/1992 | Heilman et al. | |
| 5,112,202 A | 5/1992 | Oshima et al. | |
| 5,112,295 A | 5/1992 | Zinner et al. | |
| 5,123,428 A | 6/1992 | Schwarz | |
| 5,160,338 A | 11/1992 | Vincent | |
| 5,167,611 A | 12/1992 | Cowan | |
| 5,226,429 A | 7/1993 | Kuzmak | |
| 5,250,020 A | 10/1993 | Bley | |
| 5,297,536 A | 3/1994 | Wilk | |
| 5,304,206 A | 4/1994 | Baker, Jr. et al. | |
| 5,316,543 A | 5/1994 | Eberbach | |
| 5,358,474 A | 10/1994 | Kaldany | |
| 5,415,660 A | 5/1995 | Campbell et al. | |
| 5,437,605 A | 8/1995 | Helmy | |
| 5,449,368 A | 9/1995 | Kuzmak | |
| 5,453,079 A | 9/1995 | Schwaninger | |
| 5,454,840 A * | 10/1995 | Krakovsky et al. | 607/39 |
| 5,501,703 A | 3/1996 | Holsheimer et al. | |
| 5,505,733 A | 4/1996 | Justin et al. | |
| 5,509,888 A | 4/1996 | Miller | |
| 5,518,504 A | 5/1996 | Polyak | |
| 5,540,731 A | 7/1996 | Testerman | |
| 5,569,187 A | 10/1996 | Kaiser | |
| 5,578,069 A | 11/1996 | Miner, II | |
| 5,582,580 A | 12/1996 | Buckman, Jr. et al. | |
| 5,665,065 A | 9/1997 | Colman et al. | |
| 5,676,674 A | 10/1997 | Bolanos et al. | |
| 5,690,108 A | 11/1997 | Chakeres | |
| 5,702,431 A | 12/1997 | Wang et al. | |
| 5,704,893 A | 1/1998 | Timm | |
| 5,735,887 A | 4/1998 | Barreras et al. | |
| 5,749,909 A * | 5/1998 | Schroeppel et al. | 607/33 |
| 5,769,877 A | 6/1998 | Barreras | |
| 5,771,903 A | 6/1998 | Jakobsson | |
| 5,814,020 A | 9/1998 | Gross | |
| 5,823,991 A * | 10/1998 | Shim | 604/500 |
| 5,827,286 A | 10/1998 | Incavo et al. | |
| 5,848,962 A | 12/1998 | Feindt et al. | |
| 5,858,001 A | 1/1999 | Tsals et al. | |
| 5,876,425 A | 3/1999 | Gord et al. | |
| 5,899,849 A | 5/1999 | Elist | |
| 5,900,909 A | 5/1999 | Parulski et al. | |
| 5,902,336 A | 5/1999 | Mishkin | |
| 5,910,149 A | 6/1999 | Kuzmak | |
| 5,928,195 A | 7/1999 | Malamud et al. | |
| 5,938,584 A | 8/1999 | Ardito et al. | |
| 5,938,669 A | 8/1999 | Klaiber et al. | |
| 5,978,712 A | 11/1999 | Suda et al. | |
| 5,995,874 A | 11/1999 | Borza | |
| 5,997,501 A | 12/1999 | Gross et al. | |
| 6,003,736 A | 12/1999 | Ljunggren | |
| 6,067,991 A | 5/2000 | Forsell | |
| 6,074,341 A | 6/2000 | Anderson et al. | |
| 6,077,215 A | 6/2000 | Leysieffer | |
| 6,095,968 A | 8/2000 | Snyders | |
| 6,102,887 A | 8/2000 | Altman | |
| 6,102,922 A | 8/2000 | Jakobsson et al. | |
| 6,113,574 A | 9/2000 | Spinello | |
| 6,117,067 A | 9/2000 | Gil-Vernet | |
| 6,134,470 A | 10/2000 | Hartlaub | |
| 6,135,945 A | 10/2000 | Sultan | |
| 6,162,238 A | 12/2000 | Kaplan et al. | |
| 6,185,452 B1 | 2/2001 | Schulman et al. | |
| 6,197,055 B1 | 3/2001 | Matthews | |
| 6,210,347 B1 | 4/2001 | Forsell | |
| 6,221,060 B1 | 4/2001 | Willard | |
| 6,233,474 B1 | 5/2001 | Lemelsom | |
| 6,275,737 B1 | 8/2001 | Mann | |
| 6,319,191 B1 | 11/2001 | Sayet et al. | |
| 6,346,099 B1 | 2/2002 | Altman | |
| 6,436,054 B1 | 8/2002 | Viola et al. | |
| 6,450,173 B1 | 9/2002 | Forsell | |
| 6,450,946 B1 | 9/2002 | Forsell | |
| 6,453,907 B1 | 9/2002 | Forsell | |
| 6,454,698 B1 | 9/2002 | Forsell | |
| 6,454,699 B1 | 9/2002 | Forsell | |
| 6,454,700 B1 | 9/2002 | Forsell | |
| 6,454,701 B1 | 9/2002 | Forsell | |

| | | | | | |
|---|---|---|---|---|---|
| 6,456,883 B1 | 9/2002 | Torgerson et al. | 2003/0125605 A1 | 7/2003 | Forsell |
| 6,460,543 B1 | 10/2002 | Forsell | 2003/0125768 A1 | 7/2003 | Forsell |
| 6,461,292 B1 | 10/2002 | Forsell | 2003/0144648 A1 | 7/2003 | Forsell |
| 6,461,293 B1 | 10/2002 | Forsell | 2003/0163029 A1 | 8/2003 | Sonnenschein et al. |
| 6,463,935 B1 | 10/2002 | Forsell | 2003/0208247 A1 | 11/2003 | Spinelli et al. |
| 6,464,628 B1 | 10/2002 | Forsell | 2003/0233143 A1 | 12/2003 | Gharib et al. |
| 6,470,892 B1 | 10/2002 | Forsell | 2004/0024285 A1 | 2/2004 | Muckter |
| 6,471,635 B1 | 10/2002 | Forsell | 2004/0034275 A1 | 2/2004 | Forsell |
| 6,475,136 B1 | 11/2002 | Forsell | 2004/0068299 A1 | 4/2004 | Laske et al. |
| 6,475,137 B1 | 11/2002 | Elist | 2004/0089313 A1 | 5/2004 | Utley et al. |
| 6,482,145 B1 | 11/2002 | Forsell | 2004/0098113 A1 | 5/2004 | Forsell et al. |
| 6,503,189 B1 | 1/2003 | Forsell | 2004/0102804 A1 | 5/2004 | Chin |
| 6,572,585 B2 | 6/2003 | Choi | 2004/0122526 A1 | 6/2004 | Imran |
| 6,589,229 B1 | 7/2003 | Connelly et al. | 2004/0122527 A1 | 6/2004 | Imran |
| 6,638,208 B1 | 10/2003 | Natarajan et al. | 2004/0147871 A1 | 7/2004 | Burnett |
| 6,638,303 B1 | 10/2003 | Campbell | 2004/0162568 A1 | 8/2004 | Saadat et al. |
| 6,659,936 B1 | 12/2003 | Furness et al. | 2004/0177918 A1 | 9/2004 | Murata et al. |
| 6,678,561 B2 | 1/2004 | Forsell | 2004/0249451 A1 | 12/2004 | Lu et al. |
| 6,689,085 B1 | 2/2004 | Rubenstein et al. | 2004/0260316 A1 | 12/2004 | Knudson et al. |
| 6,709,385 B2 | 3/2004 | Forsell | 2005/0038484 A1 | 2/2005 | Knudson et al. |
| 6,740,075 B2 | 5/2004 | Lebel et al. | 2005/0055025 A1 | 3/2005 | Zacouto et al. |
| 6,772,011 B2 | 8/2004 | Dolgin | 2005/0060030 A1 | 3/2005 | Lashinski et al. |
| 6,895,280 B2 | 5/2005 | Meadows et al. | 2005/0075697 A1 | 4/2005 | Olson et al. |
| 6,911,002 B2 | 6/2005 | Fierro | 2005/0222678 A1 | 10/2005 | Lashinski et al. |
| 6,915,165 B2 | 7/2005 | Forsell | 2005/0240229 A1 | 10/2005 | Whitehurst et al. |
| 6,948,918 B2 | 9/2005 | Hansen | 2005/0245957 A1 | 11/2005 | Starkebaum et al. |
| 6,953,429 B2 | 10/2005 | Forsell | 2005/0261712 A1 | 11/2005 | Balbierz et al. |
| 6,960,233 B1 | 11/2005 | Berg et al. | 2005/0266042 A1 | 12/2005 | Tseng |
| 6,979,351 B2 | 12/2005 | Forsell et al. | 2005/0267405 A1 | 12/2005 | Shah |
| 7,011,624 B2 | 3/2006 | Forsell | 2005/0267596 A1 | 12/2005 | Chen et al. |
| 7,017,583 B2 | 3/2006 | Forsell | 2006/0025855 A1 | 2/2006 | Lashinski et al. |
| 7,043,295 B2 | 5/2006 | Starkebaum | 2006/0069414 A1 | 3/2006 | Imran et al. |
| 7,066,922 B2 | 6/2006 | Angel et al. | 2006/0127246 A1 | 6/2006 | Forsell |
| 7,108,686 B2 | 9/2006 | Burke et al. | 2006/0142635 A1 | 6/2006 | Forsell |
| 7,207,936 B2 | 4/2007 | Forsell | 2006/0149124 A1 | 7/2006 | Forsell |
| 7,235,044 B2 | 6/2007 | Forsell | 2006/0167539 A1 | 7/2006 | Mcewan |
| 7,238,165 B2 | 7/2007 | Vincent | 2006/0224177 A1 | 10/2006 | Finitsis |
| 7,250,037 B2 | 7/2007 | Shermer et al. | 2006/0229688 A1 | 10/2006 | McClure et al. |
| 7,311,690 B2 | 12/2007 | Burnett | 2006/0257446 A1 | 11/2006 | Tropsha et al. |
| 7,338,437 B2 | 3/2008 | Forsell | 2007/0015959 A1 | 1/2007 | Forsell |
| 7,367,938 B2 | 5/2008 | Forsell | 2007/0038232 A1 | 2/2007 | Kraemer |
| 7,371,208 B2 | 5/2008 | Forsell | 2007/0049790 A1 | 3/2007 | Wagner et al. |
| 7,390,296 B2 | 6/2008 | Mische | 2007/0073099 A1 | 3/2007 | Forsell |
| 7,395,822 B1 | 7/2008 | Burton et al. | 2007/0092862 A1 | 4/2007 | Gerber |
| 6,929,625 B2 | 8/2008 | Forsell | 2007/0156204 A1 | 7/2007 | Denker et al. |
| 7,407,479 B2 | 8/2008 | Forsell | 2007/0167670 A1 | 7/2007 | Coleman et al. |
| 7,407,481 B2 | 8/2008 | Forsell | 2007/0193632 A1 | 8/2007 | Shu |
| 7,442,165 B2 | 10/2008 | Forsell | 2007/0204924 A1 | 9/2007 | Delgiacco et al. |
| 7,455,663 B2 | 11/2008 | Bikovsky | 2007/0225802 A1 | 9/2007 | Forsell |
| 7,569,050 B2 | 8/2009 | Moberg et al. | 2007/0232848 A1 | 10/2007 | Forsell |
| 7,621,863 B2 | 11/2009 | Forsell | 2007/0233019 A1 | 10/2007 | Forsell |
| 7,648,455 B2 | 1/2010 | Forsell | 2007/0250020 A1 | 10/2007 | Kim et al. |
| 7,666,132 B2 | 2/2010 | Forsell | 2007/0265675 A1 | 11/2007 | Lund et al. |
| 2001/0011543 A1 | 8/2001 | Forsell | 2008/0004487 A1 | 1/2008 | Haverfiled |
| 2002/0022759 A1 | 2/2002 | Forsell | 2008/0045783 A1 | 2/2008 | Forsell |
| 2002/0028980 A1 | 3/2002 | Thierfelder et al. | 2008/0051718 A1 | 2/2008 | Kavazov et al. |
| 2002/0040208 A1 | 4/2002 | Flaherty et al. | 2008/0086179 A1 | 4/2008 | Sharma |
| 2002/0055711 A1 | 5/2002 | Lavi et al. | 2008/0103544 A1 | 5/2008 | Weiner |
| 2002/0072698 A1 | 6/2002 | Chiang et al. | 2008/0200753 A1 | 8/2008 | Forsell |
| 2002/0095139 A1 | 7/2002 | Keogh et al. | 2008/0214888 A1 | 9/2008 | Shalom |
| 2002/0095164 A1 | 7/2002 | Andreas | 2008/0269548 A1 | 10/2008 | Vecchiotti et al. |
| 2002/0151922 A1 | 10/2002 | Hogendijk et al. | 2008/0275296 A1 | 11/2008 | Forsell |
| 2002/0165575 A1 | 11/2002 | Saleh | 2009/0018388 A1 | 1/2009 | Forsell |
| 2003/0009221 A1 | 1/2003 | Forsell | 2009/0054725 A1 | 2/2009 | Forsell |
| 2003/0014010 A1 | 1/2003 | Carpenter et al. | 2009/0240100 A1 | 9/2009 | Forsell |
| 2003/0014086 A1 | 1/2003 | Sharma | 2009/0240294 A1 | 9/2009 | Forsell |
| 2003/0021822 A1 | 1/2003 | Lloyd | 2009/0247817 A1 | 10/2009 | Forsell |
| 2003/0032855 A1 | 2/2003 | Shahinpoor | 2009/0247818 A1 | 10/2009 | Forsell |
| 2003/0032857 A1 | 2/2003 | Forsell | 2009/0248033 A1 | 10/2009 | Forsell |
| 2003/0050591 A1 | 3/2003 | McHale | 2009/0250068 A1 | 10/2009 | Forsell |
| 2003/0055442 A1 | 3/2003 | Laufer et al. | 2009/0254106 A1 | 10/2009 | Forsell |
| 2003/0060893 A1 | 3/2003 | Forsell | 2010/0145138 A1 | 6/2010 | Forsell |
| 2003/0066536 A1 | 4/2003 | Forsell | 2010/0145139 A1 | 6/2010 | Forsell |
| 2003/0069547 A1 | 4/2003 | Gonon | 2010/0217067 A1 | 8/2010 | Forsell |
| 2003/0088148 A1 | 5/2003 | Forsell | 2010/0312047 A1 | 12/2010 | Forsell |
| 2003/0092962 A1 | 5/2003 | Forsell | 2010/0312048 A1 | 12/2010 | Forsell |
| 2003/0100929 A1 | 5/2003 | Forsell | 2010/0312049 A1 | 12/2010 | Forsell |
| 2003/0105385 A1 | 6/2003 | Forsell | 2010/0312050 A1 | 12/2010 | Forsell |
| 2003/0109771 A1 | 6/2003 | Forsell | 2010/0312163 A1 | 12/2010 | Forsell |

| | | | |
|---|---|---|---|
| 2010/0312164 A1 | 12/2010 | Forsell | |
| 2010/0312356 A1 | 12/2010 | Forsell | |
| 2010/0318116 A1 | 12/2010 | Forsell | |
| 2010/0318117 A1 | 12/2010 | Forsell | |
| 2010/0318118 A1 | 12/2010 | Forsell | |
| 2010/0324360 A1 | 12/2010 | Forsell | |
| 2010/0324361 A1 | 12/2010 | Forsell | |
| 2010/0324362 A1 | 12/2010 | Forsell | |
| 2010/0324591 A1 | 12/2010 | Forsell | |
| 2010/0331614 A1 | 12/2010 | Forsell | |
| 2010/0331615 A1 | 12/2010 | Forsell | |
| 2010/0331616 A1 | 12/2010 | Forsell | |
| 2010/0331617 A1 | 12/2010 | Forsell | |
| 2010/0331945 A1 | 12/2010 | Forsell | |
| 2010/0332000 A1 | 12/2010 | Forsell | |
| 2011/0009894 A1 | 1/2011 | Forsell | |
| 2011/0009896 A1 | 1/2011 | Forsell | |
| 2011/0009897 A1 | 1/2011 | Forsell | |
| 2011/0015473 A1 | 1/2011 | Forsell | |
| 2011/0015474 A1 | 1/2011 | Forsell | |
| 2011/0040143 A1 | 2/2011 | Forsell | |

FOREIGN PATENT DOCUMENTS

| | | |
|---|---|---|
| DE | 199 03 246 | 8/2000 |
| EP | 0102548 | 3/1984 |
| EP | 01 343 40 | 3/1985 |
| EP | 0 200 286 | 11/1986 |
| EP | 0300552 | 1/1989 |
| EP | 0378251 | 7/1990 |
| EP | 0412191 | 2/1991 |
| EP | 0 583 012 | 2/1994 |
| EP | 0611561 | 9/1994 |
| EP | 0626154 | 11/1994 |
| EP | 0626154 A1 | 11/1994 |
| EP | 0876808 | 11/1998 |
| EP | 1 004 330 | 5/2000 |
| EP | 1 033 412 | 9/2000 |
| EP | 1 072 238 | 1/2001 |
| EP | 1 514 526 | 3/2005 |
| EP | 1563814 | 8/2005 |
| EP | 1563886 | 8/2005 |
| EP | 1 586 283 | 10/2005 |
| EP | 1 598 030 | 11/2005 |
| EP | 1598030 | 11/2005 |
| EP | 1 681 041 | 7/2006 |
| EP | 1 878 452 | 1/2008 |
| EP | 1 913 880 | 4/2008 |
| FR | 2688693 | 9/1993 |
| FR | 2692777 | 12/1993 |
| FR | 27565485 | 6/1998 |
| FR | 2 797 181 | 2/2001 |
| FR | 2797181 | 2/2001 |
| GB | 8 856 74 | 12/1961 |
| GB | 1194358 | 6/1970 |
| GB | 2 163 655 | 3/1986 |
| WO | 84/01282 | 4/1984 |
| WO | 94/27504 | 12/1994 |
| WO | 96/01597 | 1/1996 |
| WO | 96/11036 | 4/1996 |
| WO | WO 9639932 | 12/1996 |
| WO | 97/41799 | 11/1997 |
| WO | WO 98/50099 | 11/1998 |
| WO | 99/18885 | 4/1999 |
| WO | 00/09047 | 2/2000 |
| WO | 00/09048 | 2/2000 |
| WO | WO 00/09048 | 2/2000 |
| WO | 00/15158 | 3/2000 |
| WO | WO 00/16686 | 3/2000 |
| WO | 0112078 | 2/2001 |
| WO | WO 01/12108 | 2/2001 |
| WO | WO 01/45487 | 6/2001 |
| WO | WO 01/45590 | 6/2001 |
| WO | 01/47431 | 7/2001 |
| WO | 0147434 | 7/2001 |
| WO | 0147435 | 7/2001 |
| WO | WO 01/47575 | 7/2001 |
| WO | WO 0147434 | 7/2001 |
| WO | WO 0147439 | 7/2001 |
| WO | WO 01/58391 | 8/2001 |
| WO | WO 0154615 | 8/2001 |
| WO | WO 01/67964 | 9/2001 |
| WO | 02/40083 | 5/2002 |
| WO | WO 02/38217 | 5/2002 |
| WO | WO 02/053210 | 7/2002 |
| WO | WO 02/058563 | 8/2002 |
| WO | 02/087657 | 11/2002 |
| WO | WO 02/100481 | 12/2002 |
| WO | WO 03/002192 | 1/2003 |
| WO | WO 03/033054 | 4/2003 |
| WO | 2004/012806 | 2/2004 |
| WO | WO 2004/018037 | 3/2004 |
| WO | WO 2004/019765 | 3/2004 |
| WO | WO 2004/060171 | 7/2004 |
| WO | WO 2004/071684 | 8/2004 |
| WO | WO 2004/101029 | 11/2004 |
| WO | WO 9806358 | 2/2005 |
| WO | WO 2005/072169 | 8/2005 |
| WO | WO 2005/105003 | 11/2005 |
| WO | WO 2006/122285 | 11/2006 |
| WO | WO 2006/134106 | 12/2006 |
| WO | WO 2007/017880 | 2/2007 |
| WO | WO 2007/041795 | 4/2007 |
| WO | WO 2007/051563 | 5/2007 |
| WO | WO 2007/109759 | 9/2007 |
| WO | WO 2007/137026 | 11/2007 |
| WO | WO 2007/149555 | 12/2007 |
| WO | WO 2008/135988 | 11/2008 |
| WO | WO 2009/010799 | 1/2009 |
| WO | WO 2009 096854 | 8/2009 |
| WO | WO 2009/096865 | 8/2009 |
| WO | WO 2009/096868 | 8/2009 |
| WO | WO 2009/115645 | 9/2009 |

OTHER PUBLICATIONS

European Search Report, dated Sep. 14, 2006, for EP 05010107.0.
Examination Report, dated Nov. 4, 2008, in European Patent Application No. 05010107.0.
International Search Report for International Application PCT/SE01/00309, dated Jul. 20, 2001.
U.S. Appl. No. 12/865,061.
"NPC-102 N Medical Angioplasty Sensor" web page at www.novassensor.com/catalog/NPC_102.html.
Webster's II New River side University, 1984, pp. 573,1000.
Publication No. EP 1568338A2, dated Aug. 31, 2005, for European Patent Application No. 05010107.0.
U.S. Appl. No. 11/988,450, Forsell.
U.S. Appl. No. 09/373,224, Forsell.
U.S. Appl. No. 13/080,118, Forsell.
U.S. Appl. No. 13/122,809, Forsell.
U.S. Appl. No. 13/122,825, Forsell.
U.S. Appl. No. 13/122,907, Forsell.
U.S. Appl. No. 13/123,019, Forsell.
U.S. Appl. No. 13/123,025, Forsell.
U.S. Appl. No. 13/123,037, Forsell.
U.S. Appl. No. 13/123,041, Forsell.
U.S. Appl. No. 13/123,082, Forsell.
U.S. Appl. No. 13/123,151, Forsell.
U.S. Appl. No. 13/123,182, Forsell.
U.S. Appl. No. 13/123,197, Forsell.
U.S. Appl. No. 13/123,145, Forsell.
U.S. Appl. No. 13/123,183, Forsell.
U.S. Appl. No. 13/123,231, Forsell.
U.S. Appl. No. 13/123,232, Forsell.
U.S. Appl. No. 13/123,255, Forsell.
U.S. Appl. No. 13/123,261, Forsell.
U.S. Appl. No. 13/123,284, Forsell.
U.S. Appl. No. 13/123,330, Forsell.
U.S. Appl. No. 13/123,394, Forsell.
U.S. Appl. No. 13/123,402, Forsell.
U.S. Appl. No. 13/123,425, Forsell.
U.S. Appl. No. 13/123,436, Forsell.
U.S. Appl. No. 13/123,446, Forsell.
U.S. Appl. No. 13/123,536, Forsell.
U.S. Appl. No. 13/123,537, Forsell.

U.S. Appl. No. 13/123,583, Forsell.
U.S. Appl. No. 13/123,586, Forsell.
U.S. Appl. No. 13/123,587, Forsell.
U.S. Appl. No. 13/123,667, Forsell.
International Search Report for PCT/SE2010/050091, mailed May 6, 2010.

International Search Report for PCT/SE2010/050092, mailed May 6, 2010.

* cited by examiner

CONTROLLED PENILE PROSTHESIS

This application is a continuation of U.S. patent application Ser. No. 10/203,440, filed Oct. 16, 2002, now abandoned which is the U.S. National Phase of International Application No. PCT/SE01/00309, filed Feb. 14, 2001, which designated the U.S. and which claims the benefit of Provisional Application Ser. No. 60/182,189, filed Feb. 14, 2000, and Provisional Application Ser. No. 60/182,205, filed Feb. 14, 2000, the entire content of which is hereby incorporated by reference in this application.

The present invention relates to a male sexual impotence treatment prosthesis apparatus, comprising an operable penile prosthesis implantable in the cavities of the corpora cavernosa of a patient's penile tissue to provide erect penile condition, when the prosthesis is operated.

Male sexual impotence is a widespread problem. Many different solutions to this problem have been tried. In accordance with a prior system currently practised a hydraulic inflatable/contractible silicon prosthesis is implanted in the cavities of the corpora cavernosa of the penis. In fluid connection with this prosthesis is a reservoir implanted retroperitonially and a pump therefore in the scrotum. By manually pumping the pump the prosthesis is filled with fluid from the reservoir to achieve erect penile condition or is emptied of fluid, which returns to the reservoir, to achieve flaccid penile condition. However, there are several more or less severe disadvantages of this solution. A problem that often occurs is that thick, hard fibrosis is created around the pump which makes the system useless sooner or later.

Another solution to achieve erection is to restrict the blood flow leaving the penis. For example, U.S. Pat. Nos. 4,829,990, 4,958,630 and 5,048,511 disclose two hydraulically operated inflatable cuffs wrapped around the respective crura or penile exit veins. A disadvantage of such a solution is that it involves complicated surgery. U.S. Pat. No. 4,828,544 discloses another example on this solution, in which an artificial fistula system is surgically implanted and provides a primary fistula between the femoral artery and the femoral vein and a secondary fistula for leading blood from the primary fistula to the penis. An inflatable balloon engages the primary fistula between the secondary fistula and the vein. The balloon is in fluid connection with a manually compressible reservoir implanted in the scrotum. Again, implantation of this artificial fistula system requires delicate surgery.

Yet another solution is to inject a substance in the penile vein system to achieve erection. However, injections are painful and complicated for the patient.

Various impotence treatment devices in which fluid is distributed from a reservoir to an inflatable implanted prosthesis are disclosed in U.S. Pat. Nos. 3,855,122, 3,954,102, 4,009,711, 4,201,202, 4,235,227, 4,318,396 and 5,250,020.

U.S. Pat. No 4,424,807 discloses another solution in which inflatable hydraulic cylindrical elements are implanted relatively deep into the corpus cavernosum.

The object of the present invention to provide a simple male sexual impotence treatment prosthesis apparatus which is conveniently controlled by the patient.

This object is obtained by an apparatus of the kind described initially, which is characterised in that a source of energy is provided, and a control device operable from outside the patient's body is provided for controlling the source of energy to release energy for use in connection with the operation of the prosthesis, when the prosthesis is implanted.

As a result, the advantage is achieved that the prosthesis can be operated without need for touching subcutaneously implanted components of the apparatus. Furthermore, the apparatus of the invention provides simple and effective control of the energy supplied to implanted components of the apparatus which ensures an extended and reliable functionality of the apparatus, possibly for the rest of the patient's natural life, and at least many years.

Generally, the prosthesis is adapted to control the penis to change, preferably steplessly, between flaccid and erect penile condition. This gives the advantage that the patient is enabled to make fine adjustments of the prosthesis to achieve the desired erection without feeling pain.

The control device may also control the prosthesis. The control device may comprise an internal control unit, preferably including a microprocessor, implanted in the patient for controlling the prosthesis. The control device may further comprise an external control unit outside the patient's body, wherein the internal control unit is programmable by the external control unit, for example for controlling the prosthesis over a short period of time. Alternatively, the internal control unit may control the prosthesis over time in accordance with an activity schedule program, which may be adapted to the patient's needs. For example to avoid a too long duration of the penis in erect condition.

Conveniently, the external control unit may load the internal control unit with data in accordance with a loading mode only authorized for a doctor. For specialized controls of the implanted prosthesis, the external control unit may control the internal control unit in accordance with a doctor mode only authorized for the doctor. For simple controls of the implanted prosthesis, the external control unit may control the internal control unit in accordance with a patient mode permitted for the patient. Thus, by using the external control unit in accordance with different modes it is possible to have certain functions of the implanted prosthesis controlled by the patient and other more advanced functions controlled by the doctor, which enables a flexible post-operation treatment of the patient.

The control device may be adapted to control the source of energy to release energy, for instance to intermittently release energy in the form of a train of energy pulses, for direct use in connection with the operation of the prosthesis. In accordance with a suitable embodiment the control device controls the source of energy to release electric energy, and the apparatus further comprises an implantable capacitor for producing the train of energy pulses from the released energy. In this case the term "direct" is used to mean, on one hand, that the released energy is used while it is being released by the control device, on the other hand, that the released energy may be somewhat delayed, in the order of seconds, by for instance an energy stabiliser before being used in connection with the operation of the prosthesis. The prosthesis may be operable in non-manual, a non-magnetic or non-mechanical manner by use of the released energy.

In accordance with a preferred embodiment of the invention, the apparatus comprises implantable electrical components including at least one, or only one single voltage level guard and a capacitor or accumulator, wherein the charge and discharge of the capacitor or accumulator is controlled by use of the voltage level guard. As a result, there is no need for any implanted current detector and/or charge level detector for the control of the capacitor, which makes the apparatus simple and reliable.

Generally, the apparatus further comprises an operation device implantable in the patient for operating the prosthesis, wherein the control device controls the operation device to operate the prosthesis. The control device may directly power the operation device with energy released from the source of energy and/or power other energy consuming components of the apparatus to be implanted. In this case the term "directly" is used to mean, on one hand, that the operation device is powered with released energy while the latter is being released by the control device, on the other hand, that the released energy may be somewhat delayed, in the order of seconds, by for instance an energy stabiliser before powering the operation device. The advantage of directly using energy as it is released is that the apparatus can be of a very simple design and the few components involved makes the apparatus reliable.

It should be understood that the energy consuming parts of the apparatus for example a motor or pump may be or may not be energised with the unchanged wirelessly transmitted energy as this being transmitted as well as being or not being energised with energy different than the transmitted energy for example transformed into electrical energy but still directly used for energising the energy consuming parts of the apparatus as the transmitted energy is transmitted. Alternatively the energy consuming parts of the apparatus may be energised from a implanted source of energy or storage device, which still may be loaded with wireless energy. In all these aspects it is preferable to be able to wirelessly control the release of energy and get an feedback of the result of the performed function of the device. Direct use of transmitted energy may be unrelaible without a feedback what has happened, has the energy reached it's goal?

The prosthesis may be non-inflatable, i.e. with no hydraulic fluid involved for the adjustments of the prosthesis. This eliminates problems with fluid leaking from the prosthesis.

The operation device may comprise hydraulic means and at least one valve for controlling a fluid flow in the hydraulic means. The control device may suitably comprise a wireless remote control for controlling the valve. The prosthesis may comprise hydraulic means and the operation device may comprise a reservoir forming a fluid chamber with a variable volume connected to the hydraulic means. The operation device may distribute fluid from the chamber to the hydraulic means by reduction of the volume of the chamber and withdraw fluid from the hydraulic means to the chamber by expansion of the volume of the chamber.

In accordance with a first main aspect of the invention, the source of energy is external to the patient's body and the control device controls the source of energy to release wireless energy. The external source of energy may be of any conceivable kind, such as a nuclear source of energy or a chemical source of energy.

An energy storage device, preferably an electric accumulator, may be implanted in the patient for storing the wireless energy released from the external source of energy. The electric accumulator may comprise at least one capacitor or at least one rechargeable battery, or a combination of at least one capacitor and at least one rechargeable battery. Alternatively, a battery may be implanted in the patient for supplying electric energy to implanted electric energy consuming components of the apparatus, in addition to the supply of wireless energy. Where the control device comprises an implantable control unit the electronic circuit thereof and the prosthesis may be directly powered with transformed wireless energy, or energy from either the implanted energy storage device or battery.

In accordance with a second main aspect of the invention, the wireless energy is directly used for operation of the prosthesis, i.e. the prosthesis is operated as the wireless energy is released from the external source of energy by the control device. In this case the term "directly" is used to mean, on one hand, that the prosthesis is promptly operated by using the released energy whithout first storing the latter, on the other hand, that the released energy may be somewhat delayed, in the order of seconds, by for instance an energy stabiliser before being used for the operation of the prosthesis. As a result, a very simple control of the prosthesis is achieved and there are only a few implanted components of the apparatus. For example, there is no implanted source of energy, such as a battery, nor any implanted complicated signal control system. This gives the advantage that the apparatus will be extremely reliable.

Generally, the control device controls and directly or indirectly powers the operation device with wireless energy released from the source of energy and/or powers other implanted energy consuming components of the apparatus.

In a first particular embodiment in accordance with the first and second main aspects of the invention, the operation device comprises a motor, preferably an electric motor, which may have electrically conductive parts made of plastics. The motor may include a rotary motor, wherein the control device is adapted to control the rotary motor to rotate a desired number of revolutions. Alternatively, the motor may include a linear motor, or a hydraulic or pneumatic fluid motor, wherein the control device is adapted to control the fluid flow through the fluid motor. Motors currently available on the market are getting smaller and smaller. Furthermore, there is a great variety of control methods and miniaturized control equipment available. For example, a number of revolutions of a rotary motor may be analyzed by a Hall-element just a few mm in size.

In a second particular embodiment in accordance with the first and second main aspects of the invention, the control device is adapted to shift polarity of the released energy to reverse the operation device. The operation device may suitably comprise an electric motor and the released energy may comprise electric energy.

In a third particular embodiment in accordance with the first and second main aspects of the invention there is a reversing device implantable in the patient for reversing the function performed by the prosthesis, i.e. to change from erect to flaccid penile condition, suitably in a stepless manner. In this connection, the control device suitably controls the reversing device, which may include a switch, to reverse the function performed by the prosthesis. The reversing device may comprise hydraulic means including a valve for shifting the flow direction of a fluid in the hydraulic means. Alternatively, the reversing device may comprise a mechanical reversing device, such as a switch or a gearbox.

Where the reversing device comprises a switch the control device suitably controls the operation of the switch by shifting polarity of released energy supplied to the switch. The switch may comprise an electric switch and the source of energy may supply electric energy for the operation of the switch. The switch mentioned above may comprise an electronic switch or, where applicable, a mechanical switch.

In accordance with the third particular embodiment, the operation device preferably comprises a motor, wherein the reversing device reverses the motor.

In a fourth particular embodiment in accordance with the first and second main aspects of the invention, the prosthesis comprises hydraulic means, for example including an expansible/contractible cavity for fluid. Preferably, the operation device is adapted to conduct hydraulic fluid in the hydraulic means, and comprises a motor, a valveless fluid conduit connected to the hydraulic means of the prosthesis, and a reservoir for fluid, wherein the reservoir forms part of the conduit. The operation device suitably comprises a pump operated by the motor. All of the hydraulic components involved are preferably devoid of any non-return valve. This is of great advantage, because with valves involved there is always a risk of malfunction due to improperly working valves, especially when long time periods pass between valve operations. The reservoir may form a fluid chamber with a variable volume, and the pump may distribute fluid from the chamber to the hydraulic means of the prosthesis by reduction of the volume of the chamber and withdraw fluid from the hydraulic means to the chamber by expansion of the volume of the chamber.

In accordance with a third main aspect of the invention, the source of energy is implantable in the patient. Thus, when the source of energy is implanted in a patient the control device controls it from outside the patient's body to release energy. This solution is advantageous for embodiments of the apparatus that have a relatively high consumption of energy which cannot be satisfied by direct supply of wireless energy.

The implantable source of energy may comprise an accumulator, preferably an electric source of energy, such as a battery having a lifetime of at least 10 years.

In accordance with a fourth main aspect of the invention, the apparatus comprises a switch implanted in the patient for directly or indirectly switching the operation of the prosthesis and an internal source of energy, such as a battery, implanted in the patient for supplying energy for the operation of the prosthesis, wherein the switch directly or indirectly affects the supply of energy from the internal source of energy. This solution is advantageous for embodiments of the apparatus that have a relatively high energy consumption which cannot be met by direct supply of wireless energy.

In a first particular embodiment in accordance with the fourth main aspect of the invention, the switch switches between an off mode, in which the internal source of energy is not in use, and an on mode, in which the internal source of energy supplies energy for the operation of the prosthesis. In this case, the switch is conveniently operated by the wireless energy released from the external source of energy to switch between the on and off modes. The control device, preferably comprising a wireless remote control, may control the external source of energy to release the wireless energy. The advantage of this embodiment is that the lifetime of the implanted source of energy, such as a battery, can be significantly prolonged, since the implanted source of energy does not supply energy when the switch is in its off mode.

In a second particular embodiment in accordance with the fourth main aspect of the invention, the control device comprises a wireless remote control for controlling the internal source of energy. In this case, the switch is operable by the wireless energy from the external source of energy to switch between an off mode, in which the internal source of energy and remote control are not in use, and a standby mode, in which the remote control is permitted to control the internal source of energy to supply energy for the operation of the prosthesis.

In a third particular embodiment in accordance with the fourth main aspect of the invention, the apparatus further comprises an energy transforming device implanted in the patient for transforming the wireless energy into storable energy, wherein the internal source of energy is capable of storing the storable energy. The internal source of energy preferably comprises an electric accumulator, at least one capacitor or at least one rechargeable battery, or a combination of at least one capacitor and at least one rechargeable battery. In this case, the switch switches from an off mode, in which the internal source of energy is not in use, to an on mode, in which the internal source of energy supplies energy for the operation of the prosthesis.

The control device, preferably comprising a wireless remote control, may control the switch to switch between the on and off modes.

Alternatively, in this third particular embodiment an energy storage device may be implanted in the patient for storing the storable energy instead of the internal source of energy, wherein the switch is operable by energy from the implanted energy storage device to switch between an off mode, in which the internal source of energy is not in use, and an on mode, in which the internal source of energy supplies energy for the operation of the prosthesis. In this case, the control device (the wireless remote control) controls the energy storage device to operate the switch.

The internal source of energy preferably comprises an electric source of energy, such as an accumulator or a battery having a lifetime of at least 10 years. However, other kinds of sources are also conceivable, such as a nuclear source of energy or a chemical source of energy.

The above first, second, third and fourth particular embodiments described in connection with the first and second main aspects of the invention are also applicable in accordance with the third main aspect of the invention, i.e. where the source of energy is to be implanted, and in accordance with the fourth main aspect of the invention, i.e. where the apparatus comprises an implantable switch.

All of the above embodiments may be combined with at least one implantable sensor for sensing at least one physical parameter of the patient, wherein the control device may control the prosthesis in response to signals from the sensor. For example, the sensor may directly or indirectly sense ejaculation or the pressure against the prosthesis or the pressure in the urethra or any other important physical parameter. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor.

Advantageously, the sensor may sense ejaculation and the prosthesis may make the penis flaccid in response to the sensor sensing that ejaculation has occurred.

Where the control device comprises an internal control unit to be implanted in the patient, the internal control unit may suitably directly control the prosthesis in response to signals from the sensor. In response to signals from the sensor, for example pressure or any other important physical parameter, the internal control unit may send information thereon to outside the patient's body. The control unit may also automatically control the prosthesis in response to signals from the sensor, such as signals corresponding to ejaculation. For example, the control unit may control the prosthesis to make the penis flaccid in response to the sensor sensing an abnormally high pressure against the prosthesis.

Where the control device comprises an external control unit outside the patient's body, the external control unit may, suitably directly, control the prosthesis in response to signals from the sensor. The external control unit may store information on the physical parameter sensed by the sensor and may be manually operated to control the prosthesis based on the stored information. In addition, there may be at least one implantable sender for sending information on the physical parameter sensed by the sensor.

An external data communicator may be provided outside the patient's body and an internal data communicator to be implanted in the patient may be provided for communicating with the external data communicator. The internal data communicator may feed data related to the patient, or related to the prosthesis, back to the external data communicator. Alternatively or in combination, the external data communicator may feed data to the internal data communicator. The internal data communicator may suitably feed data related to at least one physical signal of the patient.

The apparatus may comprise an implantable energy transforming device, wherein the control device releases electric energy and the energy transforming device transforms the electric energy into kinetic energy for, preferably direct, operation of the prosthesis. Suitably, an implantable stabiliser, such as a capacitor or a rechargeable accumulator, or the like, may be provided for stabilising the electric energy released by the control device. In addition, the control device may control the source of energy to release energy for a determined time period or in a determined number of energy pulses. Finally, the prosthesis may be non-inflatable.

All of the above embodiments are preferably remote controlled. Thus, the control device advantageously comprises a wireless remote control transmitting at least one wireless control signal for controlling the prosthesis. With such a remote control it will be possible to adapt the function of the apparatus to the patient's need.

The wireless remote control may be capable of obtaining information on the condition of the prosthesis and of controlling the prosthesis in response to the information. Also, The remote control may be capable of sending information related to the prosthesis from inside the patient's body to the outside thereof.

In a particular embodiment of the invention, the wireless remote control comprises at least one external signal transmitter or transceiver and at least one internal signal receiver or transceiver implantable in the patient. In another particular embodiment of the invention, the wireless remote control comprises at least one external signal reciever or transceiver and at least one internal signal transmitter or transceiver implantable in the patient.

The remote control may transmit a carrier signal for carrying the control signal, wherein the carrier signal is frequency, amplitude or frequency and amplitude modulated and is digital, analog or digital and analog. Also the control signal used with the carrier signal may be frequency amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

In all of the above solutions, the control device advantageously releases energy from the source of energy in a non-invasive, magnetic, non-magnetic, mechanical or non-mechanical manner.

The control device may release magnetic, electromagnetic, kinetic, sonic or thermal energy, or non-magnetic, non-sonic, non-thermal, non-electromagnetic or non-kinetic energy.

The control device may be activated in a manual or non-manual manner to control the source of energy to release energy.

The operation device may be powered by magnetic energy, non-magnetic energy, electromagnetic energy, non-electromagnetic energy, kinetic energy, non-kinetic energy, thermal energy or non-thermal energy. However, preferably the operation device comprises an electrical operation device.

Typically the apparatus of the invention comprises an adjustment device for adjusting the prosthesis between erect and flaccid penile conditions. The adjustment device may be adapted to mechanically adjust the prosthesis. Alternatively, the adjustment device may be adapted to hydraulically adjust the prosthesis by using hydraulic means which is devoid of hydraulic fluid of the kind having a viscosity that substantially increases when exposed to heat or a magnetic field, i.e. the hydraulic fluid would not become more viscous when exposed to heat or influenced by magnetic forces.

The above-presented embodiments of the invention may be modified in accordance with the following suggestions. The released energy may comprise electric energy and an implantable capacitor having a capacity less than 0,1 µF may be provided for producing the above-mentioned train of energy pulses.

An implantable motor or pump may be provided for operating the penile prosthesis, wherein the control device is adapted to control the source of energy to directly power the motor or pump with the released energy. Specifically, the control device may be adapted to release wireless energy in the form of a magnetic field or electromagnetic waves (excluding radio waves) for direct power of the motor or pump, as the wireless energy is being released. Where a pump is used it preferably is not a plunger type of pump.

Generally, the wireless energy comprises a signal.

The apparatus may further comprise implantable energy transforming device for transforming wireless energy directly or indirectly into energy different than the wireless energy, for operation of the penile prosthesis. For example, the motor or pump may be powered by the transformed energy.

The energy transforming device may transform the wireless energy in the form of sound waves, preferably directly, into electric energy for operation of the penile prosthesis. The energy transforming device may comprise a capacitor adapted to produce electric pulses from the transformed electric energy.

The motor mentioned in the present specification may also be directly powered with wirelessly transmitted electromagnetic or magnetic energy in the form of signals, as the energy is transmitted. Furthermore, all the various functions of the motor and associated components described in the present specification may be used where applicable.

Preferable the present invention provides an a male sexual impotence treatment prosthesis, comprising an prosthesis device implanted in the corpora cavernosa of the patients penis, who suffers from impotence and an adjustment device which temporarely achieve an ereccted status of the penis and an powered operation device which is able to perform a reversible function to adjust said adjustment device.

In another embodiment of the invention the male sexual impotence treatment apparatus, comprising a hydraulic adjustment device, and further comprising a reservoir implantable in the patient and containing hydraulic fluid, and a conduit providing fluid connection between the reservoir and the hydraulic adjustment device, characterised in that the operation device being adapted to operate the hydraulic adjustment device by distributing hydraulic fluid through the conduit between the reservoir and the hydraulic adjustment device, the conduit and hydraulic adjustment device being devoid of any non-return valve to permit free flow of hydraulic fluid in both directions in the conduit.

Alternatively, or in combination with a powered operation device, the servo means may be used, which enables manual manipulation without need for strong manipulation forces. The servo means may comprise hydraulic means, electric control means, magnetic means, or mechanical means, which may be activated by manual manipulating means. Using a servo system will save the use of force when adjusting the adjustment device, which may be of importance in many applications.

The term "servo means" encompasses the normal definition of a servo mechanism, i.e. an automatic device that controls large amounts of power by means of very small amounts of power, but may alternatively or additionally encompass the definition of a mechanism that transfers a weak force acting on a moving element having a long stroke into a strong force acting on another moving element having a short stroke. The servo means may comprise a motor, preferably an electric motor, which may be reversible and/or include a gearing.

In accordance with another particular embodiment of the invention, the operation device comprises a pump for pumping fluid between the reservoir and the adjustment device. A mechanical solution is proposed in which it is possible to pump fluid from the reservoir to the adjustment device and vice versa just by pushing an activation member in one direction. The pump preferably comprises a first activation member for activating the pump to pump fluid from the reservoir to the adjustment device, and a second activation member for activating the pump to pump fluid from the adjustment device to the reservoir. At least one of the first and second activation members may be operable by manual manipulation, preferably to permit manual pushing, pulling or rotation thereof in one direction, or by a device powered magnetically, hydraulically, or electrically (e.g. by an electric motor), or be operable by a combination of these methods. Suitably, at least one of the activation members may be adapted to operate when subjected to an external pressure exceeding a predetermined magnitude.

Another alternative is a pump pumping in only one direction and an adjustable valve to change the direction of fluid to either increase or decrease the amount of fluid in the reservoir. This valve may be manipulated either manually, mechanically, magnetically, or hydraulically.

The main embodiment of the invention described above including the reservoir may alternatively be equipped with a servo means comprising a reverse servo. The term "reverse servo" is to be understood as a mechanism that transfers a strong force acting on a moving element having a short stroke into a weak force acting on another moving element having a long stroke; i.e. the reverse function of the above-defined alternative mechanism of a normal servo mechanism. A first closed hydraulic system that controls another closed hydraulic system in which hydraulic means of the adjustment device is incorporated may be used. Minor changes in the amount of fluid in a smaller reservoir of the first system could then be transferred by the reverse servo into major changes in the amount of fluid in a larger reservoir in the second system. In consequence, the change of volume in the larger reservoir of the second system affects the hydraulic means of the adjustment device. For example, a short stroke that decreases the volume of the smaller reservoir will cause the larger reservoir to supply the adjustment device with a large amount of hydraulic fluid, which in turn results in a long mechanical adjustment stroke on the restriction device.

The great advantage of using such a reverse servo is that the larger volume system could be placed inside the abdomen or retroperitoneum where there is more space and still it would be possible to use manual manipulation means of the smaller system subcutaneously. The smaller reservoir could be controlled directly or indirectly by a fluid supply means. The fluid supply means may include another small reservoir, which may be placed subcutaneously and may be activated by manual manipulation means. Both the normal servo means and the specific reverse servo may be used in connection with all of the various components and solutions described in the present specification.

Thus, the reverse servo may be adapted to provide relative displacement between the first and second wall portions of the reservoir, suitably in response to the pressure in the reservoir, in order to change the volume of the chamber of the reservoir.

Generally, the servo means, including the reverse servo, comprises a pressure controlled servo means. The alarm mentioned above may alternatively be adapted to generate an alarm signal in response to the lapse of a predetermined time period during which the pressure controlling the servo means exceeds a predetermined high value.

The reverse servo may comprise magnetic means, electric means or manual manipulation means or a combination thereof. Preferably, however, the reverse servo comprises hydraulic means.

In accordance with a particular embodiment of the invention, the reverse servo further comprises a servo reservoir defining a chamber containing servo fluid, and the operation device comprise first and second wall portions of the servo reservoir, which are displaceable relative to each other to change the volume of the chamber of the servo reservoir. The first and second wall portions of the servo reservoir may be displaceable relative to each other by magnetic means, hydraulic means, or electric control means.

Where the reverse servo comprises hydraulic means it may further comprise a fluid supply reservoir connected to the servo reservoir in a closed system and containing a further predetermined amount of fluid. The fluid supply reservoir defines a chamber for the further predetermined amount of fluid and the operation device is adapted to change the volume of the chamber and thereby control the amount of fluid in the servo reservoir. The fluid supply reservoir comprises first and second wall portions, which are displaceable relative to each other to change the volume of the chamber of the fluid supply reservoir. Suitable, the fluid supply reservoir increases the amount of fluid in the servo reservoir in response to a predetermined first displacement of the first wall portion of the fluid supply reservoir relative to the second wall portion of the fluid supply reservoir and decreases the amount of fluid in the servo reservoir in response to a predetermined second displacement of the first wall portion of the fluid supply reservoir relative to the second wall portion of the fluid supply reservoir.

Generally, the penile prosthesis advantageously is embedded in a soft or gel-like material, such as a silicone material having hardness less than 20 Shore.

Of course, the penile prosthesis preferably is adjustable in a non-manual manner.

All the above described various components, such as the motor, pump and capacitor, may be combined in the different embodiments where applicable. Also the various functions described in connection with the above embodiments of the invention may be used in different applications, where applicable.

All the various ways of transferring energy and controlling the energy presented in the present specification may be practised by using all of the various components and solutions described.

The present invention also provides a method of treating an impotent male patient, comprising: (a) surgically implanting an operable prosthesis in the corpora cavernosa of the male patient. (b) Providing a source of energy. (c) Controlling the source of energy to release energy for use in connection with the operation of the prosthesis.

Steps (b) and (c) may further comprise providing the source of energy external to the patient's body and controlling the external source of energy from outside the patient's body to release wireless energy for use in connection with the operation of the prosthesis.

The method may further comprise (d) implanting in the patient an operation device which can adjust the prosthesis in response to supplied energy, and (f) using the released wireless energy to operate the implanted operation device to achieve erect or flaccid penile condition.

In accordance with an alternative method, there is provided a method of treating an impotent male patient, comprising the steps of placing at least two laparascopical trocars in the patient's body, inserting a tool through the trocars and using the tool to place an operable prosthesis in the cavities of the corpora cavernosa, providing a source of energy outside or inside the male patient's body, controlling the source of energy from outside the patient's body to release energy, which may comprise wireless energy where the source of energy is external to the patient's body, and using the released energy in connection with the operation of the prosthesis.

In accordance with another alternative method, there is provided a method of treating an impotent male patient, comprising the steps of placing at least two laparascopical trocars in the male patient's body, inserting a tool through the trocars and using the tool to place an operable prosthesis in the cavities of the corpora cavernosa, implanting an energy transforming device, providing an external source of energy, controlling the external source of energy to release wireless energy, and transforming the wireless energy by the energy transforming device into energy different than the wireless energy for use in connection with the operation of the prosthesis. This method may further comprise implanting a stabiliser in the patient's body to stabilize the energy transformed by the energy transforming device.

It is the primary object of the present invention to provide a simple yet effective apparatus for treating male sexual impotence. This and other objects of the invention will become clear from an inspection of the detailed description of the invention and from the appended claims.

The invention is described in more detail in the following with reference to the accompanying drawings, in which FIGS. 1 to 6 are schematic block diagrams illustrating six embodiments, respectively, of the invention, in which wireless energy released from an external source of energy is used for direct operation of a prosthesis implanted in the penile tissue of a patient;

Referring to the drawing figures, like reference numerals designate identical or corresponding elements throughout the several figures.

Figure 1:
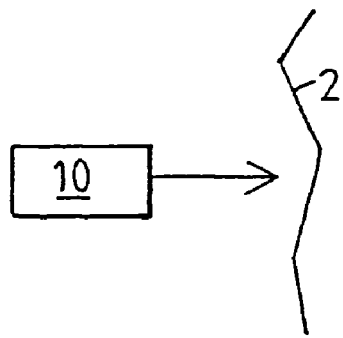
Figure 1:
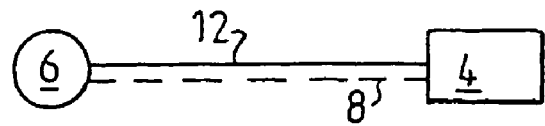

FIG. 1 schematically shows an embodiment of the male sexual impotence treatment prosthesis apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body.

The apparatus of FIG. 1 comprises an implanted operable prosthesis 4, which is placed in the cavities of the corpora cavernosa of the patient's penis. The implanted prosthesis 4 is capable of performing a reversible function, i.e. to erect the penis or to make the penis flaccid. An implanted control unit 6 controls the implanted prosthesis 4 via a control line 8 to achieve an adequate erection An external control unit 10 includes an external source of energy and a wireless remote control transmitting a control signal generated by the external source of energy. The control signal is received by a signal receiver incorporated in the implanted control unit 6, whereby the control unit 6 controls the implanted prosthesis 4 in response to the control signal. The implanted control unit 6 also uses energy from the control signal for directly operating the implanted prosthesis 4 via a power supply line 12, as the control signal is transmitted.

Figure 2:
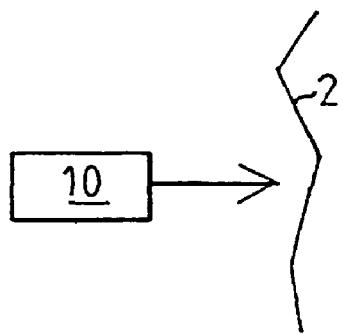
Figure 2:
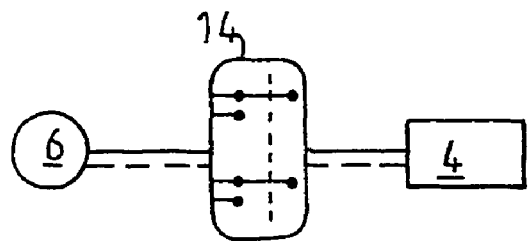

FIG. 2 shows an embodiment of the invention identical to that of FIG. 1, except that a reversing device in the form of a switch 14 also is implanted in the patient for reversing the implanted prosthesis 4. The control unit 6 uses the switch 14 to reverse the function performed by the implanted prosthesis 4. More precisely, the external control unit 10 releases energy carried by a wireless signal and the implanted control unit 6 transforms the wireless energy into a current for operating the switch 14. When the control unit 6 shifts the polarity of the current the switch 14 reverses the function performed by the implanted prosthesis 4.

Figure 3:
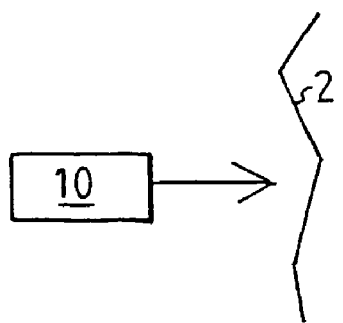
Figure 3:
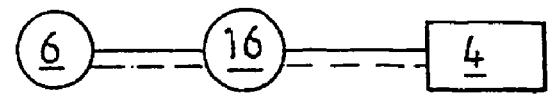

FIG. 3 shows an embodiment of the invention identical to that of FIG. 1, except that an operation device in the form of a motor 16 also is implanted in the patient. The implanted control unit 6 powers the motor 16 with wireless energy released from the external source of energy of the external control unit 10. The implanted control unit 6 controls the operation of the motor 16 in response to a control signal from the remote control of the external control unit 10.

Figure 4:
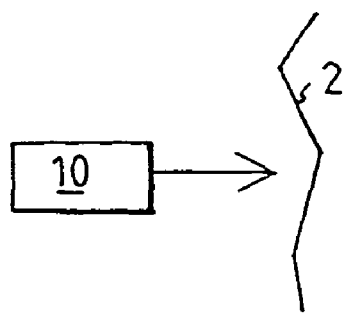
Figure 4:
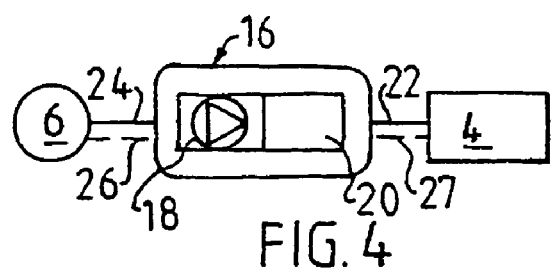

FIG. 4 shows an embodiment of the invention identical to that of FIG. 1, except that an assembly 16 including a motor/pump unit 18 and a fluid reservoir 20 also is implanted in the patient. In this case the prosthesis 4 is hydraulically operated, i.e. hydraulic fluid is pumped by the motor/pump unit 18 from the reservoir 20 through a conduit 22 to the prosthesis 4 to erect the penis, and hydraulic fluid is pumped by the motor/pump unit 16 back from the prosthesis 4 to the reservoir 20 to make the penis flaccid. The external control unit 10 releases energy carried by a wireless signal and the implanted control unit 6 transforms the wireless energy into a current, for example a current, for powering the motor/pump unit 18 via an electric power supply line 24. The implanted control unit 6 controls the motor/pump unit 16 and the prosthesis 4 via control lines 26 and 27.

Figure 5:
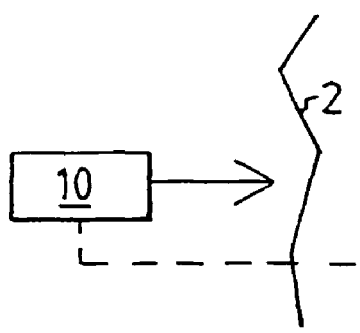
Figure 5:
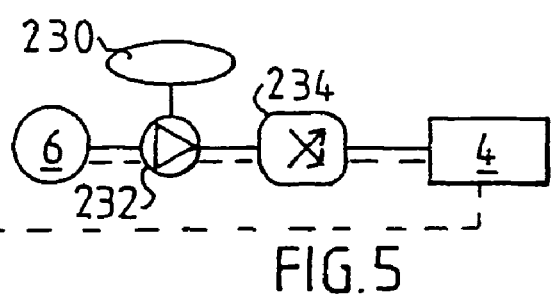

FIG. 5 shows an embodiment of the invention comprising the prosthesis 4, hydraulically operated, and the implanted control unit 6, and further comprising a hydraulic fluid reservoir 230, a motor/pump unit 232 and a reversing device in the form of a hydraulic valve shifting device 234, all of which are implanted in the patient. The motor of the motor/pump unit 232 is an electric motor.

Figure 6:
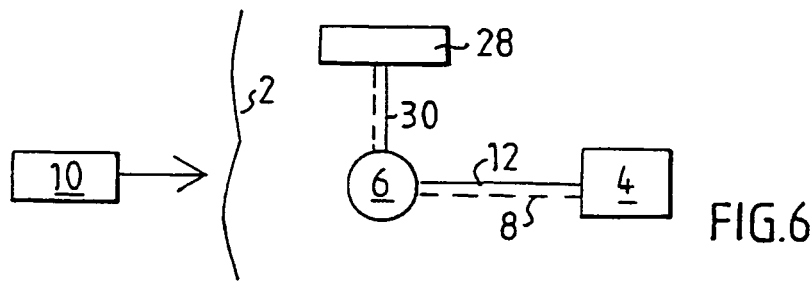

FIG. 6 shows an embodiment of the invention identical to that of FIG. 1, except that an accumulator 28 also is implanted in the patient. The control unit 6 stores energy received from the external control unit 10 in the accumulator 28. In response to a control signal from the external control unit 10 the implanted control unit 6 releases energy from the accumulator 28 via a power line 30 for the operation of the prosthesis 4.

Figure 7:
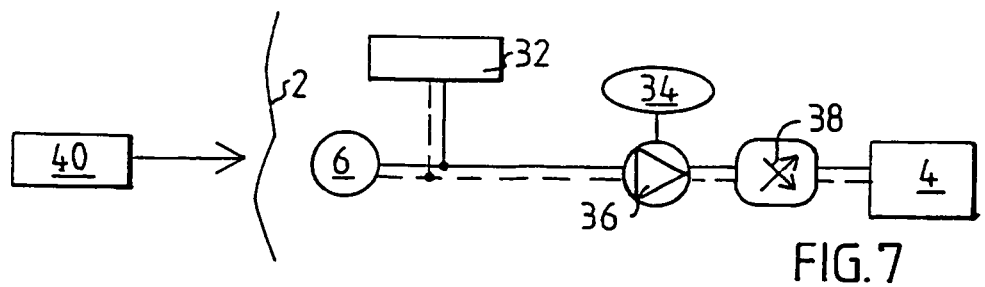
FIGS. 7 to 10 are schematic block diagrams illustrating four embodiments, respectively, of the invention, in which energy is released from an implanted source of energy.

FIG. 7 shows an embodiment of the invention comprising the prosthesis 4, hydraulically operated, and the implanted control unit 6, and further comprising a source of energy in the form of a battery 32, a hydraulic fluid reservoir 34, a motor/pump unit 36 and a reversing device in the form of a hydraulic valve shifting device 38, all of which are implanted in the patient. The motor of the motor/pump unit 36 is an electric motor. An external control unit 40 includes a wireless remote control transmitting a control signal which is received by the signal receiver incorporated in the implanted control unit 6.

In response to a control signal from the external control unit 40 the implanted control unit 6 powers the motor/pump unit 36 with energy from the battery 32, whereby the motor/pump unit 36 distributes hydraulic fluid between the reservoir 34 and the prosthesis 4. The control unit 6 controls the shifting device 38 to shift the hydraulic fluid flow direction between one direction in which the fluid is pumped by the motor/pump unit 36 from the reservoir 34 to the prosthesis 4 to erect the penis, and another opposite direction in which the fluid is pumped by the motor/pump unit 36 back from the prosthesis 4 to the reservoir 34 to make the penis flaccid.

Figure 8:
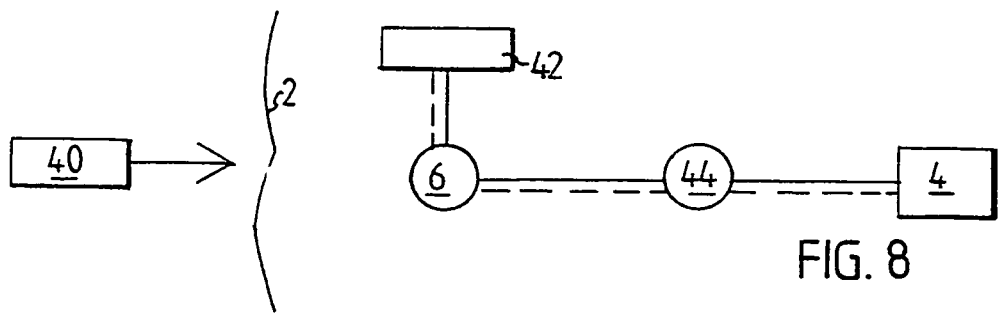

FIG. 8 shows an embodiment of the invention identical to that of FIG. 6, except that a battery 42 is substituted for the accumulator 28, the external control unit 40 of the embodiment of FIG. 5 is substituted for the external control unit 10 and an electric motor 44 is implanted in the patient for operating the prosthesis 4. In response to a control signal from the external control unit 40 the implanted control unit 6 powers the motor 44 with energy from the battery 42, whereby the motor 44 operates the prosthesis 4.

Figure 9:
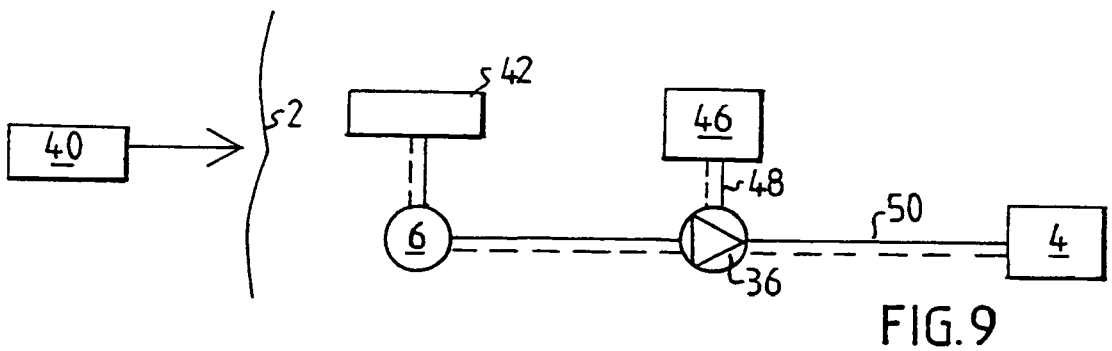

FIG. 9 shows an embodiment of the invention identical to that of FIG. 8, except that the motor/pump unit 36 of the embodiment of FIG. 7 is substituted for the motor 44 and a fluid reservoir 46 also is implanted in the patient. The reservoir 46 is via fluid conduits 48 and 50 connected to the motor/pump unit 36 and prosthesis 4, which in this case is hydraulically operated. In response to a control signal from the external control unit 40, the implanted control unit 6 powers the electric motor of the motor/pump unit 36 with energy from the battery 42, whereby the motor/pump unit 36 distributes hydraulic fluid between the fluid reservoir 46 and the prosthesis 4.

Figure 10:
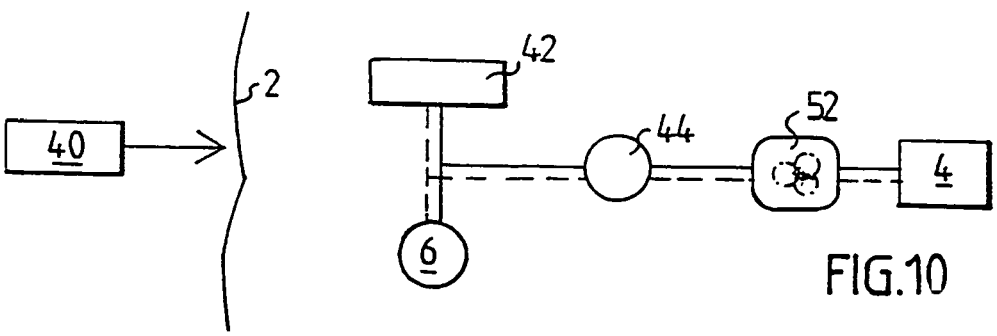

FIG. 10 shows an embodiment of the invention identical to that of FIG. 8, except that a mechanical reversing device in the form of a gearbox 52 also is implanted in the patient. The implanted control unit 6 controls the gearbox 52 to reverse the function performed by the prosthesis 4 (mechanically operated).

Figure 11:
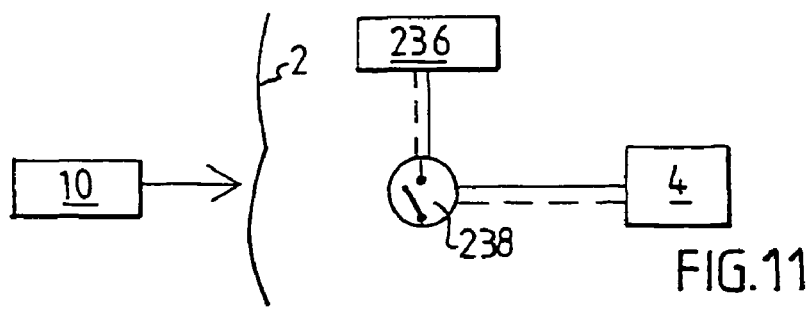
FIGS. 11 to 15 are schematic block diagrams illustrating five embodiments, respectively, of the invention, in which a switch is implanted in the patient for directly or indirectly switching the operation of the prosthesis.

FIG. 11 shows an embodiment of the invention comprising the prosthesis 4, the external control unit 10, an implanted source of energy 236 and an implanted switch 238. The switch 238 is operated by wireless energy released from the external source of energy of the external control unit 6 to switch between an off mode, in which the implanted source of energy 236 is not in use, and an on mode, in which the implanted source of energy 236 supplies energy for the operation of the prosthesis 4.

Figure 12:
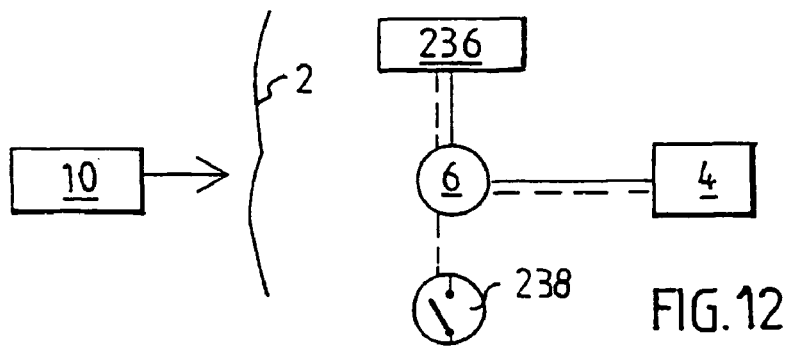

FIG. 12 shows an embodiment of the invention identical to that of FIG. 11, except that also the control unit 6 is implanted, in order to receive a control signal from the wireless remote control of the external control unit 10. The switch 238 is operated by the wireless energy from the external source of energy 10 to switch between an off mode, in which the implanted source of energy 236 and the wireless remote control of the external control unit 10 are not in use, i.e. the control unit 6 is not capable of receiving the control signal, and a standby mode, in which the wireless remote control is permitted to control the internal source of energy 236, via the implanted control unit 6, to supply energy 30 for the operation of the prosthesis 4.

Figure 13:
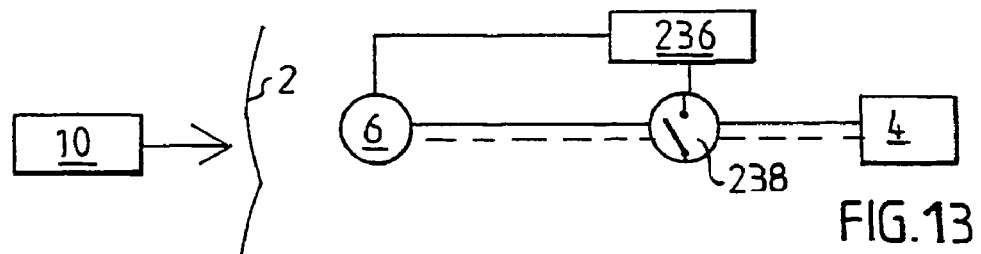

FIG. 13 shows an embodiment of the invention identical to that of FIG. 12, except that an energy transforming device for transforming the wireless energy into storable energy is incorporated in the implanted control unit 6 and that the implanted source of energy 236 is of a type that is capable of storing the storable energy. In this case, in response to a control signal from the external control unit 10, the implanted control unit 6 controls the switch 238 to switch from an off mode, in which the implanted source of energy 236 is not in use, to an on mode, in which the source of energy 36 supplies energy for the operation of the prosthesis 4.

Figure 14:
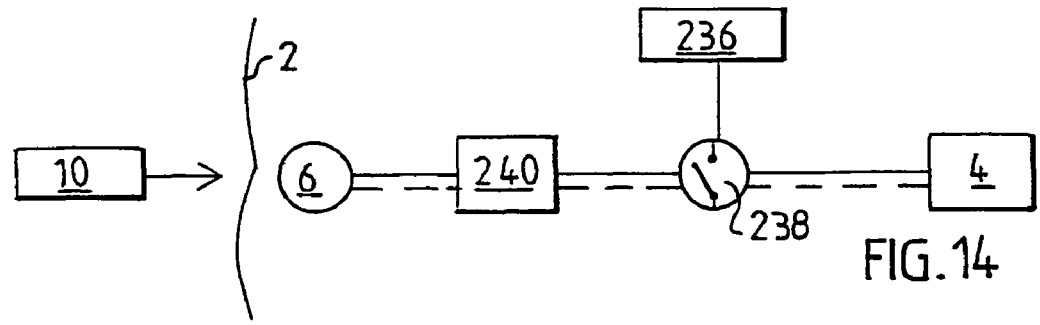

FIG. 14 shows an embodiment of the invention identical to that of FIG. 13, except that an energy storage device 240 also is implanted in the patient for storing the storable energy transformed from the wireless energy by the transforming device of the control unit 6. In this case, the implanted ontrol unit 6 controls the energy storage device 240 to operate the switch 238 to switch between an off mode, in which the implanted source of energy 236 is not in use, and an on mode, in which the implanted source of energy 236 supplies energy for the operation of the prosthesis 4.

Figure 15:
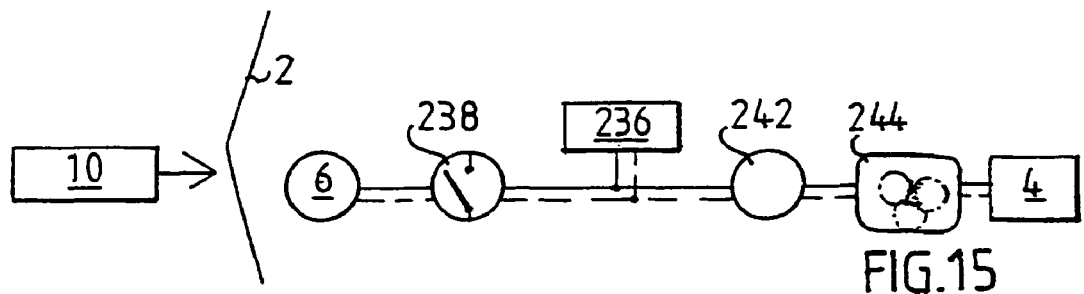

FIG. 15 shows an embodiment of the invention identical to that of FIG. 13, except that a motor 242 and a mechanical reversing device in the form of a gearbox 244 also are implanted in the patient. The implanted control unit 6 controls the gearbox 244 to reverse the function performed by the prosthesis 4 (mechanically operated), i.e. erecting the penis and making the penis flaccid.

Figure 16:
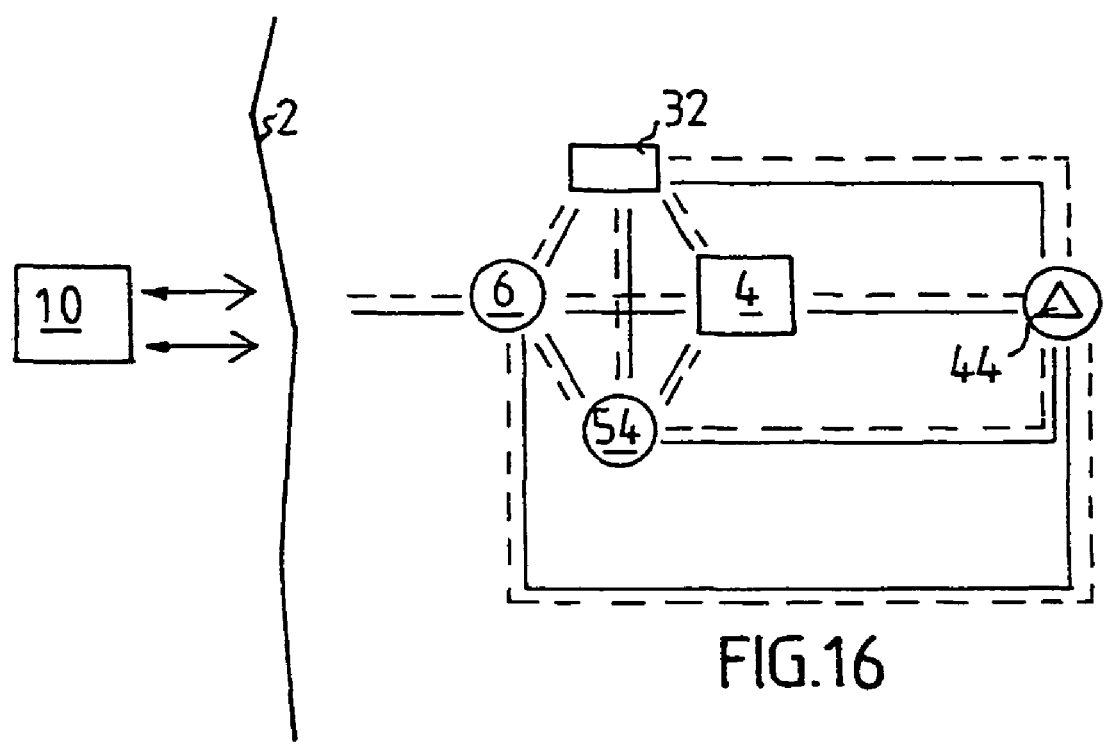
FIG. 16 is a schematic block diagram illustrating conceivable combinations of implantable components for achieving various communication options.

FIG. 16 schematically shows conceivable combinations of implanted components of the apparatus for achieving various communication possibilities. Basically, there are the implanted prosthesis 4, the implanted control unit 6 and the external control unit 10 including the external source of energy and the wireless remote control. As already described above the remote control transmits a control signal generated by the external source of energy, and the control signal is received by a signal receiver incorporated in the implanted control unit 6, whereby the control unit 6 controls the implanted prosthesis 4 in response to the control signal.

A sensor 54 may be implanted in the patient for sensing a physical parameter of the patient, such as the pressure in the stomach. The control unit 6, or alternatively the external control unit 10, may control the prosthesis 4 in response to signals from the sensor 54. A transceiver may be combined with the sensor 54 for sending information on the sensed physical parameter to the external control unit, 10. The wireless remote control of the external control unit 10 may comprise a signal transmitter or transceiver and the implanted control unit 6 may comprise a signal receiver or transceiver.

Alternatively, the wireless remote control of the external control unit 10 may comprise a signal receiver or transceiver and the implanted control unit 6 may comprise a signal transmitter or transceiver. The above transceivers, transmitters and receivers may be used for sending information or data related to the prosthesis from inside the patient's body to the outside thereof.

The motor 44 may be implanted for operating the prosthesis 4 and also the battery 32 may be implanted for powering the motor 44. The battery 32 may be equipped with a transceiver for sending information on the charge condition of the battery.

Those skilled in the art will realize that the above various embodiments according to FIGS. 1-15 could be combined in many different ways. For example, the energy operated switch 14 could be incorporated in any of the embodiments of FIGS. 4, 6, 8-10. The hydraulic shifting device 38 could be incorporated in any of the embodiments of FIGS. 4 and 9. The gearbox 52 could be incorporated in any of the embodiments of FIGS. 1, 6 and 8.

Figure 17:
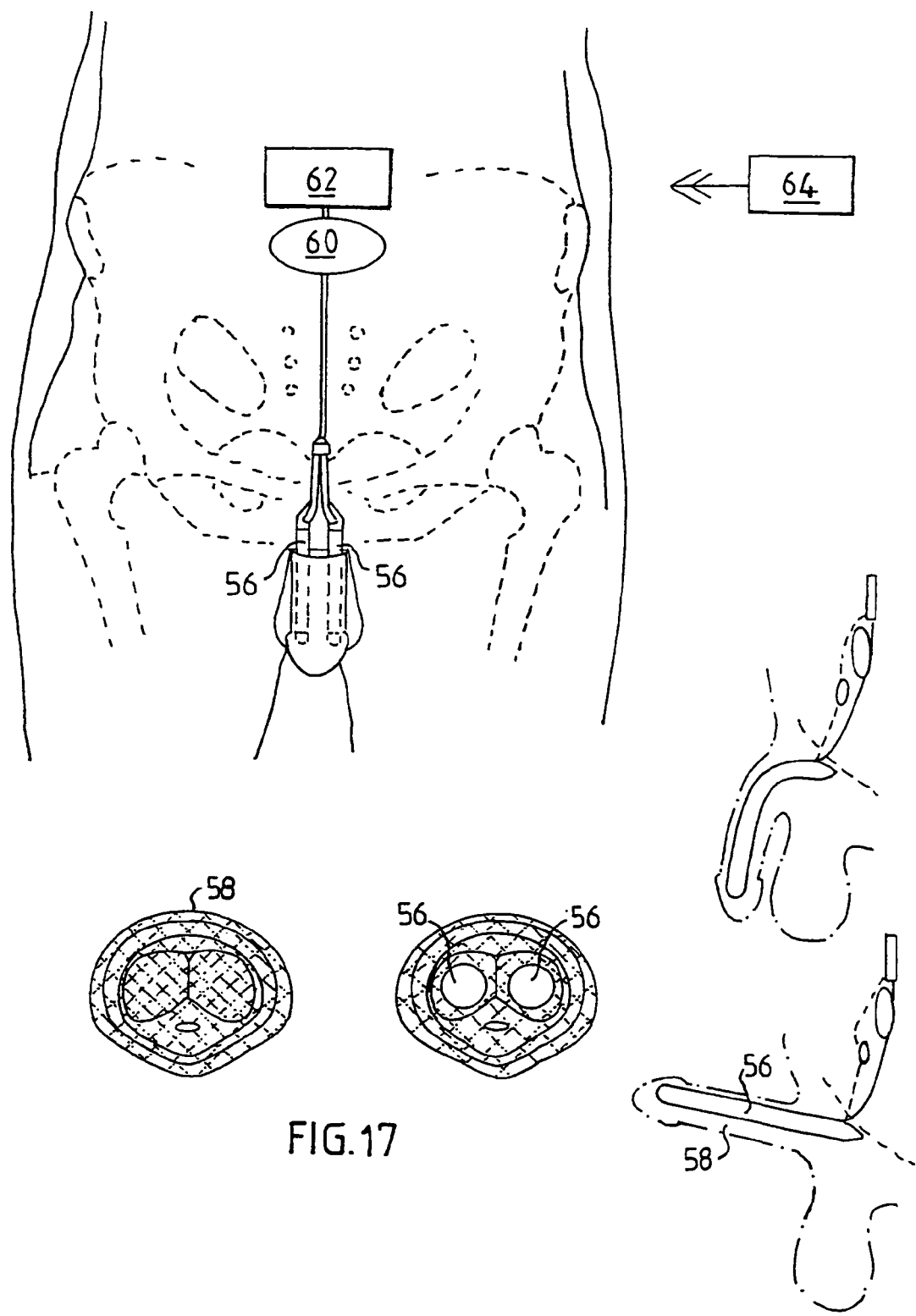
FIG. 17 illustrates the apparatus in accordance with the invention implanted in a patient.

FIG. 17 illustrates how any of the above-described embodiments of the impotence treatment prosthesis apparatus of the invention may be implanted in a patient. Thus, the apparatus comprises a prosthesis including two elongated balloon elements 56 implanted in the cavities of the corpora cavernosa of the patient's penile tissue 58, and an implanted hydraulic operation device 60 for operating the prosthesis elements 56. A control device in the form of a wireless remote control comprises an implanted control unit 62, which includes a signal receiver, for controlling the operation device 60, and an external control unit 64 including a signal transmitter for transmitting a control signal to the signal receiver of the implanted control unit 62. The implanted control unit 62 is capable of transforming signal energy from the control signal into electric energy for powering the operation device 60 and for energizing electric energy consuming implanted components of the apparatus. When the patient desires to achieve erection, he uses the external control unit 64 to activate the operation device 60 to distribute hydraulic fluid into the two balloon elements 56, whereby each element 56 is inflated and assumes the shape of a straight rod as indicated in FIG. 17.

Figure 18:
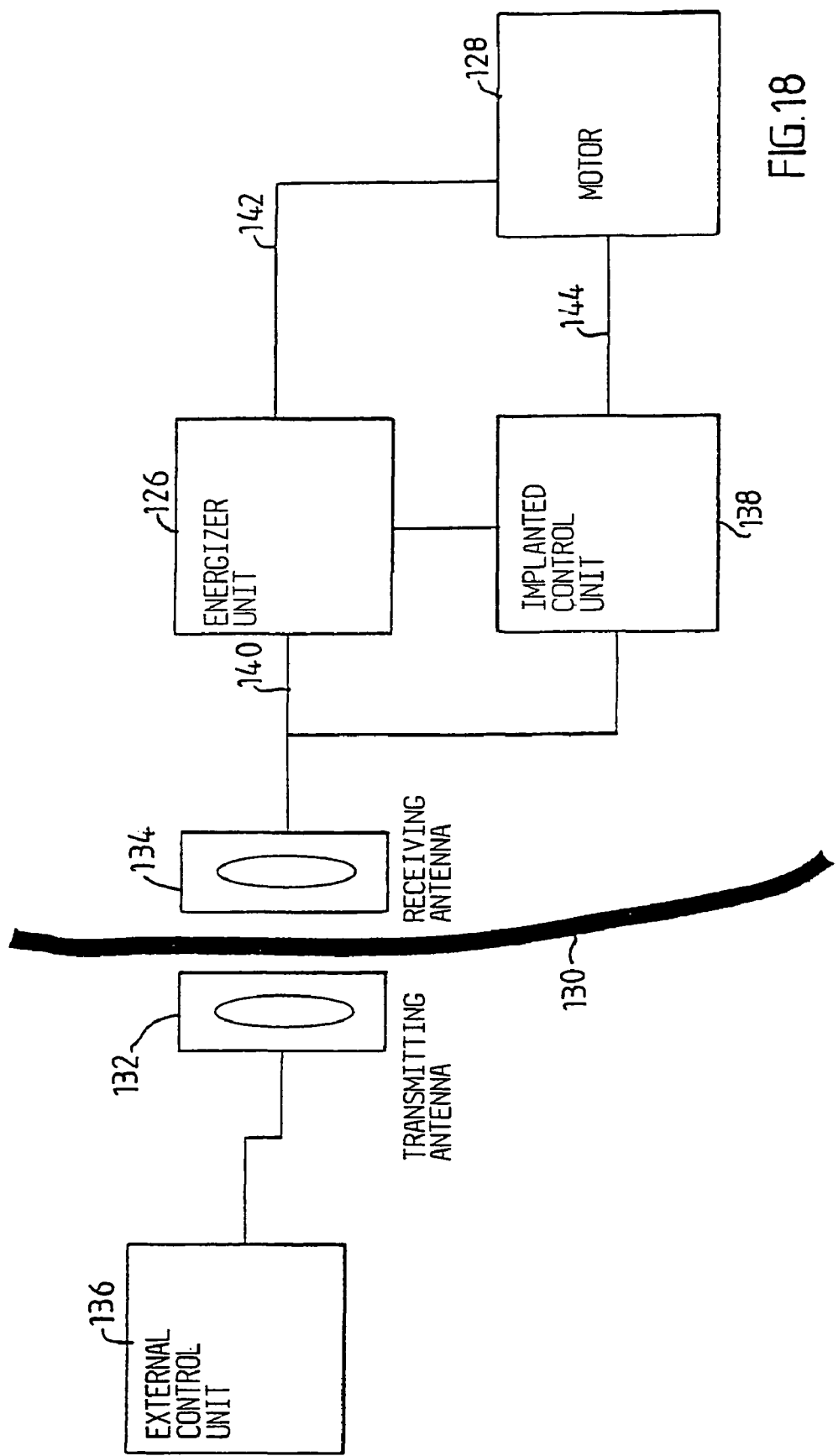
FIG. 18 is a block diagram illustrating remote control components of an embodiment of the invention.

FIG. 18 shows the basic parts of a wireless remote control of the apparatus of the invention including an electric motor 128 for operating a prosthesis, for example of the type illustrated in FIG. 17. In this case, the remote control is based on the transmission of electromagnetic wave signals, often of high frequencies in the order of 100 kHz-1 gHz, through the skin 130 of the patient. In FIG. 18, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same restriction as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send, digital information via the power amplifier and the antennas 132, 134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to activate the prosthesis to either restrict or enlarge the blood flow passageway. The microprocessor starts a command by applying a high frequency signal on the antenna 132. After a short time, when the signal has energized the implanted parts of the control system, commands are sent to restrict or enlarge the blood flow passageway in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously during a rather long time period (e.g. about 30 seconds or more). When a new restrict or enlarge step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signals received by the receiving antenna 134. The energizer unit 126 stores the energy in a power supply, such as a large capacitor, powers the control unit 138 and powers the electric motor 128 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 128 to operate the prosthesis to either erect the penis or make the penis flaccid depending on the received command code.

Alternatively, the energy stored in the power supply of the energizer unit may only be used for powering a switch, and the energy for powering the motor 128 may be obtained from another implanted power source of relatively high capacity, for example a battery. In this case the switch is adapted to connect the battery to the control unit 138 in an on mode when the switch is powered by the power supply and to keep the battery disconnected from the control unit in a standby mode when the switch is unpowered.

Figure 19:
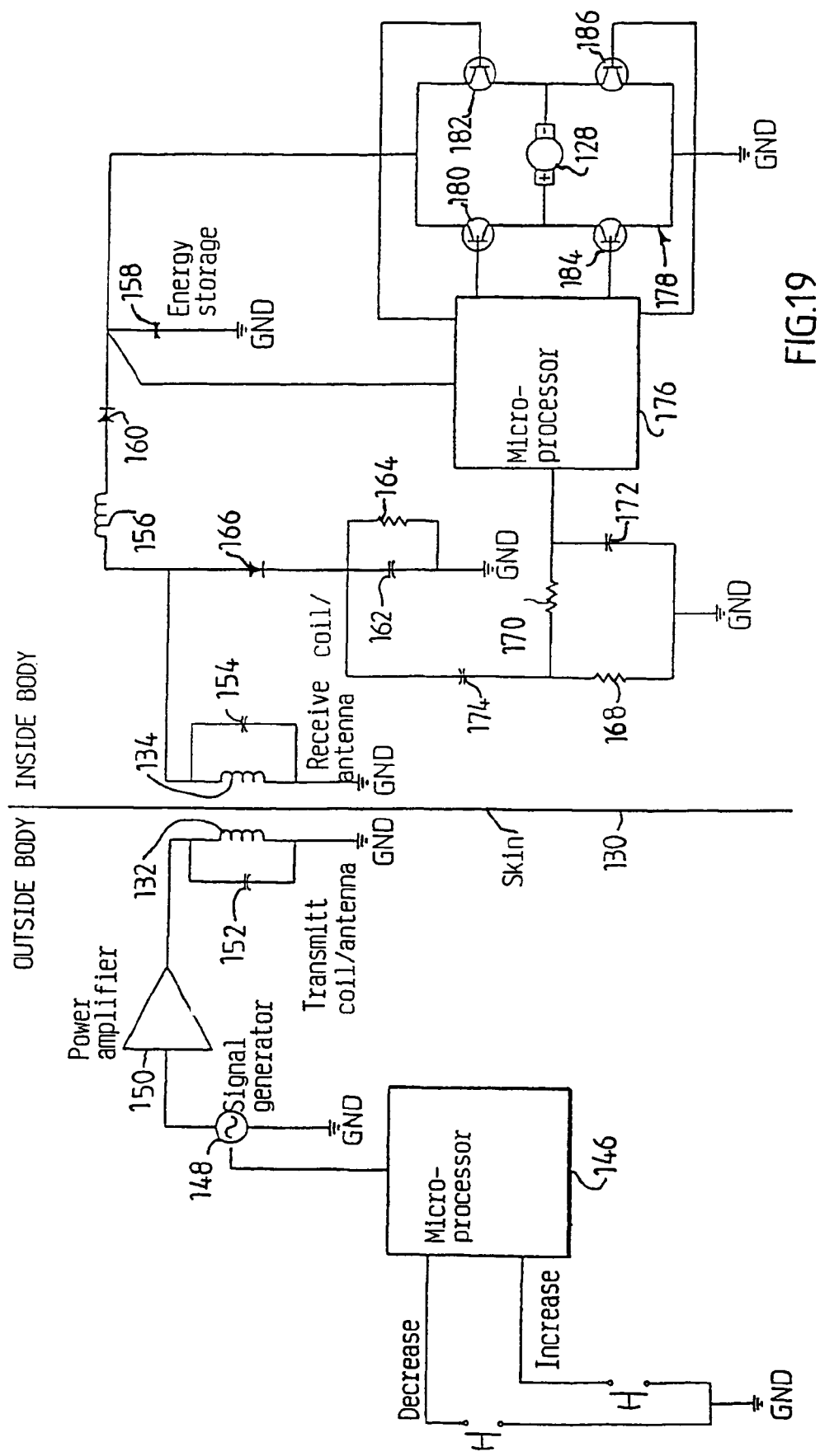
FIG. 19 is a schematic view of exemplary circuitry used for the components of the block diagram of FIG. 18.

With reference to FIG. 19, the remote control schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168, 170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 128 via an H-bridge 178 comprising transistors 180, 182, 184 and 186. The motor 128 can be driven in two opposite directions by the H-bridge 178.

The microprocessor 176 also monitors the amount of stored energy in the storage capacitor 158. Before sending signals to activate the motor 128, the microprocessor 176 checks whether the energy stored in the storage capacitor 158 is enough. If the stored energy is not enough to perform the requested operation, the microprocessor 176 waits for the received signals to charge the storage capacitor 158 before activating the motor 128.

The invention claimed is:

1. A male sexual impotence treatment prosthesis apparatus comprising:
   an operable prosthesis implantable in the cavities of the corpora cavernosa of an impotent patient to provide erect penile condition, when the prosthesis is operated;
   an external source of energy adapted to release wireless energy for use in connection with the operation of the prosthesis;
   an implantable energy transforming device for transforming the wireless energy to storable energy;
   an internal, implantable source of energy adapted to store the energy released from the external source of energy; and
   a control device operable from the outside of patient's body is provided for controlling the internal source of energy for use in connection with the operation of the prosthesis, when the prosthesis is implanted,
   wherein the apparatus further comprises an external data communicator to be provided outside the patient's body and an internal data communicator to be implanted in the patient for communicating with the external data communicator, said internal data communicator is capable of feeding data related to the patient or related to the prosthesis, back to the external data communicator and said external data communicator is capable of feeding data to said internal data communicator.

2. An apparatus according to claim 1, wherein control device is adapted to control the external source of energy to release wireless energy for use in connection with the operation of the prosthesis.

3. An apparatus according to claim 1, wherein the control device controls the prosthesis.

4. An apparatus according to claim 3, wherein the control device comprises an internal control unit implantable in the patient for controlling the prosthesis.

5. An apparatus according to claim 4, wherein the internal control unit is programmable.

6. An apparatus according to claim 5, wherein the control device comprises an external control unit intended to be outside the patient's body, the internal control unit being programmable by the external control unit.

7. An apparatus according to claim 5, wherein the internal control unit is programmable for controlling the prosthesis over time.

8. An apparatus according to claim 7, wherein the internal control unit controls the prosthesis over time in accordance with an activity schedule program.

9. An apparatus according to claim 7, wherein the internal control unit comprises a microprocessor.

10. An apparatus according to claim 6, wherein the external control unit loads the internal control unit with data in accordance with a loading mode only authorized for a doctor.

11. An apparatus according to claim 6, wherein the external control unit controls the internal control unit in accordance with a doctor mode only authorized for a doctor.

12. An apparatus according to claim 6, wherein the external control unit controls the internal control unit in accordance with a patient mode permitted for the patient.

13. An apparatus according to claim 1, wherein the implantable source of energy comprises at least one accumulator, at least one capacitor or at least one rechargeable battery, or a combination of at least one capacitor and at least one rechargeable battery.

14. An apparatus according to claim 13, wherein the implantable source of energy comprises an electric source of energy.

15. An apparatus according to claim 14, wherein the electric source of energy comprises an accumulator, or a battery having a lifetime of at least 10 years.

16. An apparatus according to claim 1, wherein the control device controls the penile prosthesis.

17. An apparatus according to claim 1, wherein the implantable source of energy comprises an accumulator.

18. An apparatus according to claim 17, wherein the accumulator comprises an electric accumulator.

19. An apparatus according to claim 18, wherein the electric accumulator comprises at least one capacitor, or a combination of at least one capacitor and at least one rechargeable battery.

20. An apparatus according to claim 1, further comprising a battery implantable in the patient for supplying electric energy to implantable electric energy consuming components of the apparatus.

21. The apparatus according to claim 1, wherein the control device is adapted to control the external source of energy to release wireless energy for direct use in connection with the operation of the penile prosthesis.

22. The apparatus according to claim 21, wherein the control device is adapted to control the external source of energy to intermittently release wireless energy in the form of a train of energy pulses for direct use in connection with the operation of the penile prosthesis.

23. The apparatus according to claim 21, wherein the penile prosthesis is operable in a non-magnetic, non-thermal or non-mechanical manner by use of said released wireless energy.

24. The apparatus according to claim 1, further comprising a switch implantable in the patient for directly or indirectly switching the operation of the penile prosthesis.

25. The apparatus according to claim 24, wherein the switch directly or indirectly affects the supply of energy from the internal source of energy.

26. The apparatus according to claim 25, wherein the switch switches between an "off" mode, in which the internal source of energy is not in use, and an "on" mode, in which the internal source of energy supplies energy for the operation of the penile prosthesis.

27. The apparatus according to claim 1, further comprising a switch implantable in the patient for directly or indirectly switching the operation of the penile prosthesis, wherein the switch is operable by the wireless energy released from the external source of energy.

28. The apparatus according to claim 27, wherein the control device controls the external source of energy to release the wireless energy.

29. The apparatus according to claim 1, wherein the control device comprises a wireless remote control.

30. The apparatus according to claim 29, wherein the wireless remote is adapted to control the internal source of energy.

31. The apparatus according to claim 30, further comprising a switch implantable in the patient for directly or indirectly switching the operation of the penile prosthesis, wherein the switch is operable by the wireless energy from the external source of energy to switch between an "off" mode, in which the internal source of energy and remote control are not in use, and a "standby" mode, in which the remote control is permitted to control the internal source of energy to supply energy for the operation of the penile prosthesis.

32. The apparatus according to claim 29, wherein the control device controls the switch to switch between the "on" and "off" modes.

33. An apparatus according to claim 1, further comprising an operation device implantable in the patient for operating the penile prosthesis.

34. An apparatus according to claim 33, wherein the control device controls the operation device to operate the penile prosthesis.

35. An apparatus according to claim 33, wherein the operation device comprises hydraulic means and at least one valve for controlling a fluid flow in the hydraulic means.

36. An apparatus according to claim 35, wherein the control device comprises a wireless remote control for controlling the valve.

37. An apparatus according to claim 34, wherein the penile prosthesis comprises hydraulic means and the operation device comprises a reservoir forming a fluid chamber with a variable volume connected to the hydraulic means, and the operation device is adapted to distribute fluid from the chamber to the hydraulic means by reduction of the volume of the chamber and to withdraw fluid from the hydraulic means to the chamber by expansion of the volume of the chamber.

38. An apparatus according to claim 1, wherein the operation device comprises a motor.

39. An apparatus according to claim 38, wherein the motor comprises a rotary motor, and the control device controls the rotary motor to rotate a desired number of revolutions.

40. An apparatus according to claim 38, wherein the motor comprises a linear motor.

41. An apparatus according to claim 38, wherein the motor comprises a hydraulic or pneumatic fluid motor, and the control device controls the fluid motor.

42. An apparatus according to claim 38, wherein the motor comprises an electric motor having electrically conductive parts made of plastics.

43. An apparatus according to claim 1, wherein the control device releases polarized energy from the internal source of energy.

44. An apparatus according to claim 34, wherein the control device shifts polarity of the released energy to reverse the operation device.

45. An apparatus according to claim 33, wherein the operation device comprises an electric motor and the released energy comprises electric energy.

46. An apparatus according to claim 1, wherein the penile prosthesis is operable to perform a reversible function.

47. An apparatus according to claim 46, further comprising a reversing device implantable in the patient for reversing the function performed by the penile prosthesis.

48. An apparatus according to claim 47, wherein the control device controls the reversing device to reverse the function performed by the penile prosthesis.

49. An apparatus according to claim 48, wherein the reversing device comprises hydraulic means including a valve for shifting the flow direction of a fluid in the hydraulic means.

50. An apparatus according to claim 48, wherein the reversing device comprises a mechanical reversing device.

51. An apparatus according to claim 50, wherein the mechanical reversing device comprises a switch.

52. An apparatus according to claim 50, wherein the reversing device comprises a gearbox.

53. An apparatus according to claim 52, wherein the reversing device comprises a switch.

54. An apparatus according to claim 53, wherein the switch of the reversing device is operable by the released energy.

55. An apparatus according to claim 54, wherein the control device controls the operation of the switch of the reversing device by shifting polarity of the released energy supplied to the switch.

56. An apparatus according to claim 55, wherein the switch comprises an electric switch and the source of energy supplies electric energy for the operation of the switch.

57. An apparatus according to claim 53, wherein the operation device comprises a motor, and the reversing device reverses the motor.

58. An apparatus according to claim 1, further comprising an operation device implantable in the patient for operating the penile prosthesis.

59. An apparatus according to claim 58, wherein the penile prosthesis comprises hydraulic means and the operation device is adapted to conduct a hydraulic fluid in the hydraulic means.

60. An apparatus according to claim 59, wherein the operation device comprises a motor.

61. An apparatus according to claim 59, wherein the operation device comprises a fluid conduit connected to the hydraulic means of the penile prosthesis, and a reservoir for fluid, the reservoir forming part of the conduit.

62. An apparatus according to claim 61, wherein the hydraulic means and conduit are devoid of any non-return valve.

63. An apparatus according to claim 61, wherein the reservoir forms a fluid chamber with a variable volume, and the operation device is adapted to distribute fluid from the chamber to the hydraulic means of the penile prosthesis by reduction of the volume of the chamber and to withdraw fluid from the hydraulic means to the chamber by expansion of the volume of the chamber.

64. An apparatus according to claim 1, further comprising at least one implantable sensor for sensing at least one physical parameter of the patient.

65. An apparatus according to claim 64, wherein the sensor is adapted to directly or indirectly sense as the physical parameter ejaculation or the pressure in the urethra.

66. An apparatus according to claim 64, wherein the control device controls the penile prosthesis in response to signals from the sensor.

67. An apparatus according to claim 66, wherein the control device comprises an internal control unit implantable in the patient, the internal control unit controlling the penile prosthesis in response to signals from the sensor.

68. An apparatus according to claim 67, wherein the control device comprises an external control unit outside the patient's body, the external control unit controlling the penile prosthesis in response to signals from the sensor.

69. An apparatus according to claim 68, wherein the external control unit stores information on the physical parameter sensed by the sensor and is manually operated to control the penile prosthesis based on the stored information.

70. An apparatus according to claim 64, further comprising at least one implantable sender for sending information on the physical parameter sensed by the sensor.

71. An apparatus according to claim 1, wherein the internal data communicator feeds data related to at least one physical signal of the patient.

72. An apparatus according to claim 1, wherein the prosthesis is adapted to control the penis to change between flaccid and erect penile condition.

73. An apparatus according to claim 72, wherein the prosthesis is operable to erect the penis or to make it flaccid.

74. An apparatus according to claim 72, wherein the prosthesis is adapted to control the penis to steplessly change between flaccid and erect penile condition.

75. An apparatus according to claim 1, wherein the control device is adapted to control the external source of energy to release wireless electric energy and the energy transforming device is adapted to transform the electric energy into kinetic energy for operation of the prosthesis.

76. An apparatus according to claim 75, wherein the prosthesis is directly operated with the kinetic energy, as the energy transforming device transforms the electric energy into the kinetic energy.

77. An apparatus according to claim 1, wherein the prosthesis is non-inflatable.

78. An apparatus according to claim 1, wherein the control device controls the internal source of energy to release energy for a determined time period.

79. An apparatus according to claim 1, wherein the control device controls the source of energy to release energy in a determined number of energy pulses.

80. An apparatus according to claim 1, wherein the control device is adapted to control the internal source of energy to release energy in a non-invasive manner.

81. An apparatus according to claim 1, wherein the control device comprises a wireless remote control for transmitting at least one wireless control signal for controlling the prosthesis.

82. An apparatus according to claim 81, wherein the remote control is capable of obtaining information on the condition of the prosthesis when the prosthesis is implanted and of controlling the prosthesis in response to the information.

83. An apparatus according to claim 81, wherein the wireless remote control comprises at least one external signal transmitter or transceiver and at least one internal signal receiver or transceiver implantable in the patient.

84. An apparatus according to claim 81, wherein the wireless remote control comprises at least one external signal receiver or transceiver and at least one internal signal transmitter or transceiver implantable in the patient.

85. An apparatus according to claims 82, wherein the remote control is capable of sending information related to the prosthesis from inside the patient's body to the outside thereof.

86. An apparatus according to claim 85, wherein the remote control controls the prosthesis in response to the information.

87. An apparatus according to any of claims 81, wherein the remote control transmits a carrier signal for carrying the control signal.

88. An apparatus according to claim 87, wherein the carrier signal is frequency, amplitude or frequency and amplitude modulated.

89. An apparatus according to claim 87, wherein the carrier signal is digital, analog or digital and analog.

90. An apparatus according to claim 87, wherein the control signal used with the carrier signal is frequency, amplitude or frequency and amplitude modulated.

91. An apparatus according to claim 81, wherein the control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

92. An apparatus according to claim 81, wherein the control signal comprises an electric, a magnetic or an electric and magnetic field.

93. An apparatus according to claims 81, wherein the control signal is digital, analog or digital and analog.

94. An apparatus according to claim 93, wherein the remote control transmits an electromagnetic carrier wave signal for carrying the digital or analog control signal.

95. An apparatus according to claims 81, wherein the control signal is transmitted in pulses by the wireless remote control.

96. An apparatus according to claim 1, further comprising an implantable stabilizer for stabilizing the energy released by the control device.

97. An apparatus according to claim 96, wherein the energy released by the control device comprises electric energy and the stabilizer comprises at least one capacitor.

98. An apparatus according to claim 1, wherein the penile prosthesis is operable by the released energy in a manual, mechanical, thermal or magnetic manner.

99. An apparatus according to claim 1, wherein the penile prosthesis is operable by the released energy in a non-manual, non-mechanical, non-thermal or non-magnetic manner.

100. An apparatus according to claim 1, wherein the control device is adapted to control the source of energy to release electric energy, and further comprising an implantable capacitor for producing the train of energy pulses from the released energy.

101. An apparatus according to claim 1, further comprising an adjustment device for adjusting the penile prosthesis, wherein the adjustment device is adapted to mechanically adjust the penile prosthesis, or adapted to hydraulically adjust the penile prosthesis by using hydraulic means which is devoid of hydraulic fluid of the kind having a viscosity that substantially increases when exposed to heat or a magnetic field.

102. An apparatus according to claim 33, wherein the operation device comprises an electrical operation device.

103. An apparatus according to claim 33, wherein the operation device is powered by magnetic energy, non-magnetic energy, electromagnetic energy, non-electromagnetic energy, kinetic energy, non-kinetic energy, thermal energy or non-thermal energy.

104. An apparatus according to claim 1, wherein the control device is activated in a manual or non-manual manner to control the source of energy to release energy.

105. An apparatus according to claim 1, further comprising implantable electrical components including at least one voltage level guard.

106. An apparatus according to claim 1, further comprising implantable electrical components including a single voltage level guard.

107. An apparatus according to claim 105, wherein the electrical components are devoid of any current detector and/or charge level detector.

108. An apparatus according to claim 105, further comprising an implantable capacitor or accumulator, wherein the charge or discharge of the capacitor or accumulator is controlled by use of the voltage level guard.

109. An apparatus according to claim 21, wherein the released energy comprises electric energy and further comprising an implantable capacitor for producing the train of energy pulses.

110. An apparatus according to claim 108, wherein the capacitor has a capacity less than 0,1 µF.

111. An apparatus according to claim 1, further comprising an implantable motor or pump for operating the penile prosthesis, wherein the control device is adapted to control the source of energy to directly power the motor or pump with the released energy.

112. An apparatus according to claim 21, wherein the wireless energy comprises electromagnetic waves excluding radio waves.

113. An apparatus according to claim 1, further comprising an implantable motor or pump for operating the penile prosthesis, wherein the control device is adapted to release wireless energy in the form of a magnetic field or electromagnetic waves for direct power of the motor or pump, as the wireless energy is being released.

114. An apparatus according to claim 113, wherein the pump is not a plunger type of pump.

115. An apparatus according to claim 1, wherein the wireless energy comprises a signal.

116. An apparatus according to claim 1, wherein the energy transforming device transforms the wireless energy in the form of sound waves into electric energy for operation of the penile prosthesis.

117. An apparatus according to claim 116, wherein the energy transforming device transforms the wireless energy in the form of sound waves directly into electric energy.

118. An apparatus according to claim 116, wherein the energy transforming device comprises a capacitor.

119. An apparatus according to claim 118, wherein the capacitor is adapted to produce electric pulses from the transformed electric energy.

120. An apparatus according to claim 116, further comprising an implantable motor or pump for operating the penile prosthesis, wherein the motor or pump is powered by the transformed energy.

121. An apparatus according to claim 1, wherein the penile prosthesis is adjustable in a non-manual manner.

122. An apparatus according to claim 1, wherein the penile prosthesis is embedded in a soft or gel-like material.

123. An apparatus according to claim 122, wherein the penile prosthesis is embedded in a silicone material having hardness less than 20 Shore.

124. An apparatus according to claim 21, further comprising an activatable source of energy implantable in the patient, wherein the internal source of energy is activated by wireless energy released from the external source of energy, to supply energy which is used in connection with the operation of the prosthesis.

125. An apparatus according to claim 1, wherein the prosthesis is reversibly adjustable between flaccid and erect penile conditions by displacing a hydraulic fluid into or from the cavities of copora cavernosa.

126. An apparatus according to claim 18, wherein the electric accumulator comprises at least one rechargeable battery.

* * * * *